United States Patent [19]
Spengler et al.

[11] Patent Number: 5,876,972
[45] Date of Patent: Mar. 2, 1999

[54] NUCLEIC ACID MOLECULES CODING FOR TUMOR SUPPRESSOR PROTEINS AND METHODS FOR THEIR ISOLATION

[75] Inventors: Dietmar Spengler, Munich, Germany; Laurent Journot, Pignan, France

[73] Assignees: Max-Planck-Gesellschaft zur Forderung der Wissenschaften e.V., Berlin, Germany; CNRS, Montpellier, France

[21] Appl. No.: 718,661

[22] Filed: Sep. 23, 1996

[51] Int. Cl.⁶ .............................. C12P 21/00; C12N 15/12
[52] U.S. Cl. .................. 435/69.1; 435/172.3; 435/252.3; 435/325; 435/410; 435/320.1; 536/23.5
[58] Field of Search ............................. 435/172.3, 320.1, 435/252.3, 325, 410, 69.1; 536/23.5

[56] References Cited

PUBLICATIONS

Spengler, D. et al., Nature (9 Sep. 1993) 365: 170–175.
Spengler, D. et al., 2nd International Symposium on VIP, PACAP, and Related Peptides, Oct. 4–7, 1995.

Primary Examiner—Charles L. Patterson, Jr.
Attorney, Agent, or Firm—John P. White; Cooper & Dunham LLP

[57] ABSTRACT

Described are novel proteins having the biological activity of a tumor suppressor protein and nucleic acid molecules coding for such proteins. Methods for the isolation of nucleic acid molecules encoding tumor suppressor proteins as well as nucleic acid molecules obtainable by said method are also provided. Further, vectors comprising said nucleic acid molecules wherein the nucleic acid molecules are operatively linked to regulatory elements allowing expression in prokaryotic or eukaryotic host cells can be used for the production of polypeptides encoded by said nucleic acid molecules which have tumor suppressor activity. Pharmaceutical and diagnostic compositions are provided comprising the nucleic acid molecules of the invention and/or comprising a nucleic acid molecule which is complementary to such a nucleic acid molecule. Described are also compositions which comprise polypeptides encoded by the described nucleic acid molecules which have tumor suppressor activity and/or an antibody specifically recognizing such polypeptides.

24 Claims, 15 Drawing Sheets

FIG. 1A

| | | | |
|---|---|---|---|
| 1 | MAPFRCQKCG | | |
| | KSFVTLEKFT | IHNYSHSRER | PFKCSKAECG | 40 |
| 41 | KAFVSKYKLM | RHMATHSPQK | IHQCTHCEKT | FNRKDHLKNH | 80 |
| 81 | LQTHDPNKIS | YACDDCGKKY | HTMLGYKRHL | ALHSASNGDL | 120 |
| 121 | TCGVCTLELG | STEVLLDHLK | SHAEEKANQA | PREKKYQCDH | 160 |
| 161 | CDRCFYTRKD | VRRHLVVHTG | CKDFLCQFCA | QRFGRKDHLT | 200 |
| 201 | RHTKKTHSQE | LMQENMQAGD | YQSNFQLIAP | STSFQIKVDP | 240 |
| 241 | MPPFQLGAAP | ENGLDGGLPP | EVHGLVLAAP | EEAPQPMPPL | 280 |
| 281 | EPLEPLEPLE | PLEPMQSLEP | LQPLEPMQPL | EPMQPLEPMQ | 320 |
| 321 | PLEPLEPLEP | MQPLEPMQPL | EPMQPMLPMQ | PMQPMQPMQP | 360 |
| 361 | MLPMQPMLPM | QPMQPMQPML | PMPEPSFTLH | PGVVPTSPPP | 400 |
| 401 | IILQEHKYNP | VPTSYAPFVG | MPVKADGKAF | CNVGFFEEFP | 440 |
| 441 | LQEPQAPLKF | NPCFEMPMEG | FGKVTLSKEL | LVDAVNIAIP | 480 |
| 481 | ASLEISSLLG | FWQLPPPTPQ | NGFVNSTIPV | GPGEPLPHRI | 520 |
| 521 | TCLAQQQPPP | LPPPPPLPLP | QPLPVPQPLP | QPQMQPQFQL | 560 |
| 561 | QIQPQMQLPQ | LLPQLQPQQQ | PDPEPEPEPE | PEPEPEPEPE | 600 |
| 601 | PEPEPEPEPE | PEPEEEQEEA | EEEAEEGAEE | GAEPEAQAEE | 640 |
| 641 | EEEEEEAEEP | QPEEAQIAGL | VYKKWTV    | | 667 |
| | | ****       | | |

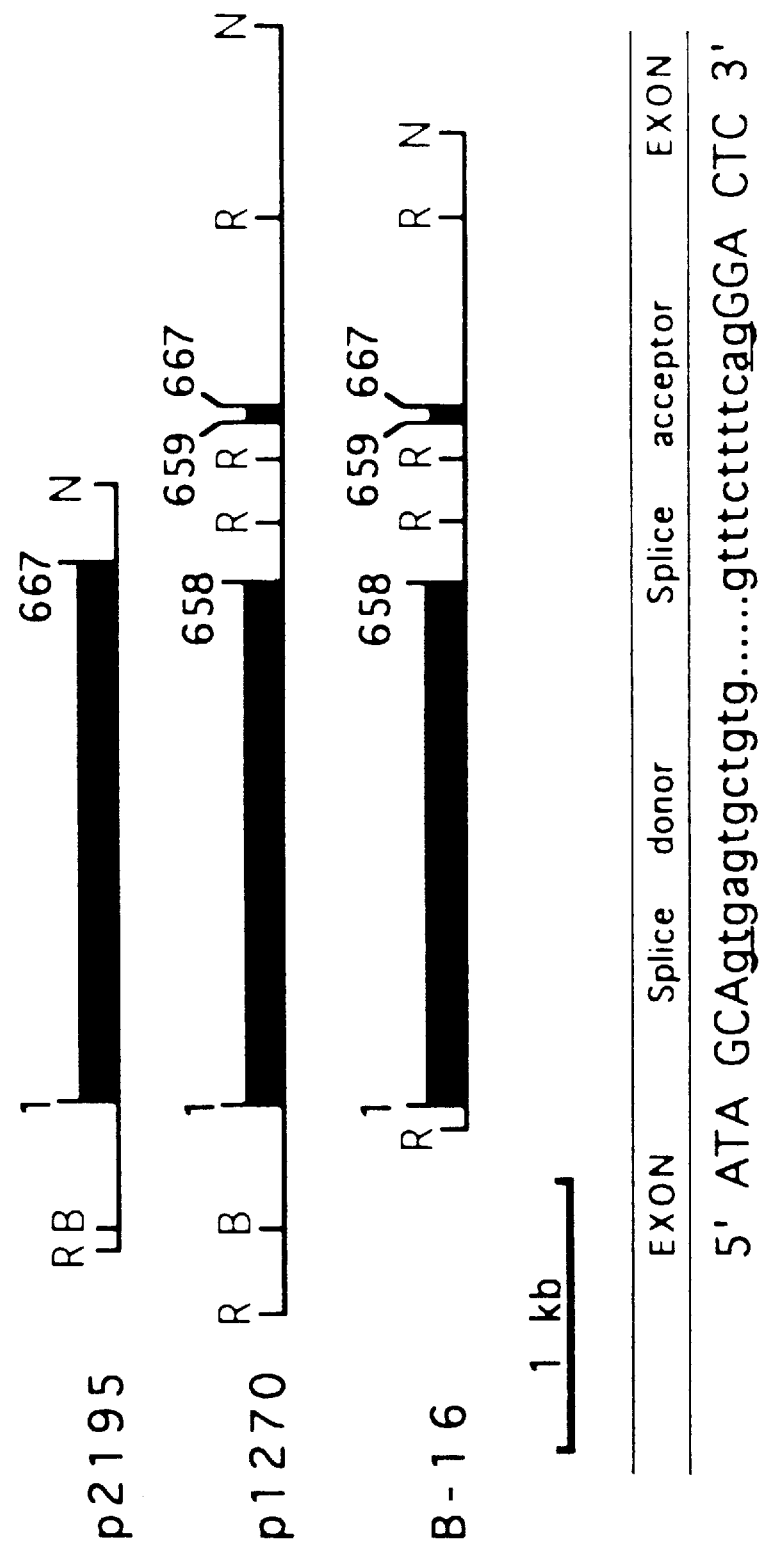

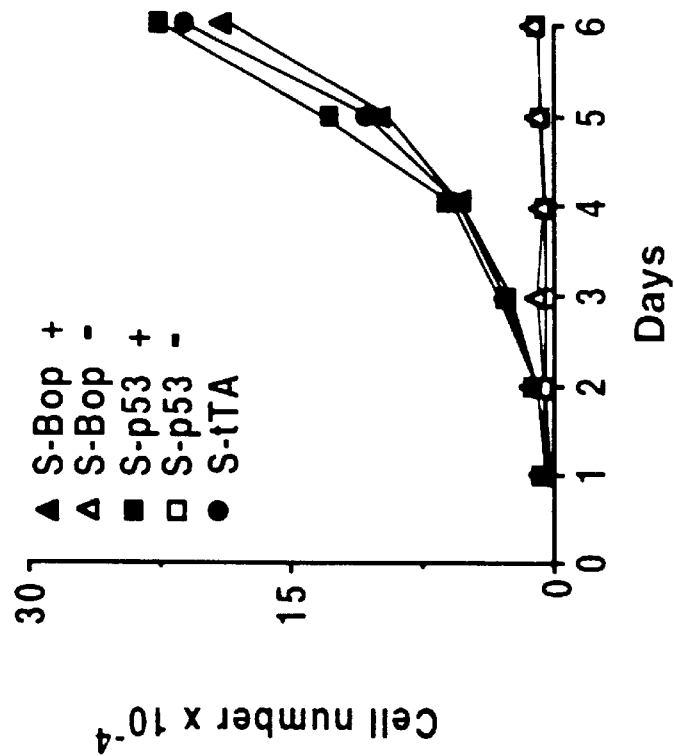
FIG. 2A-2 Saos-2
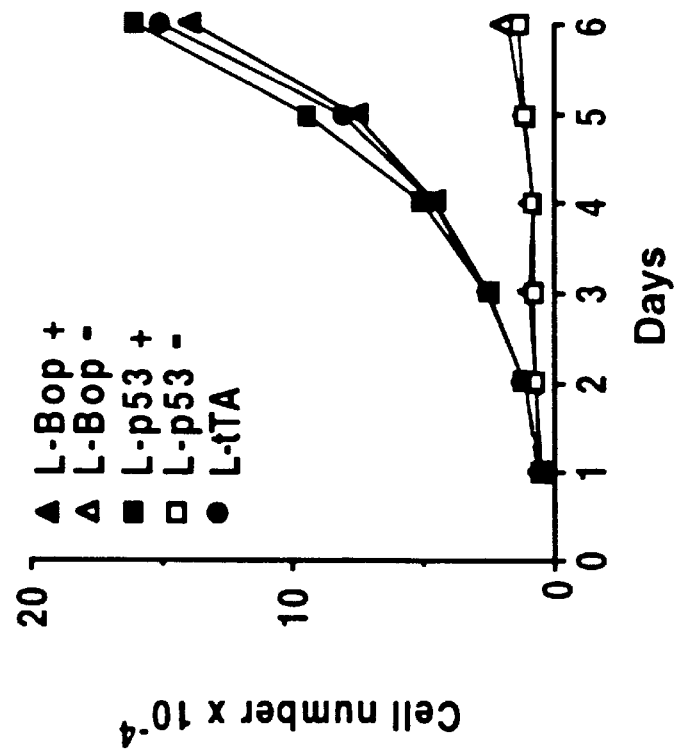
FIG. 2A-1 LLC-PK1

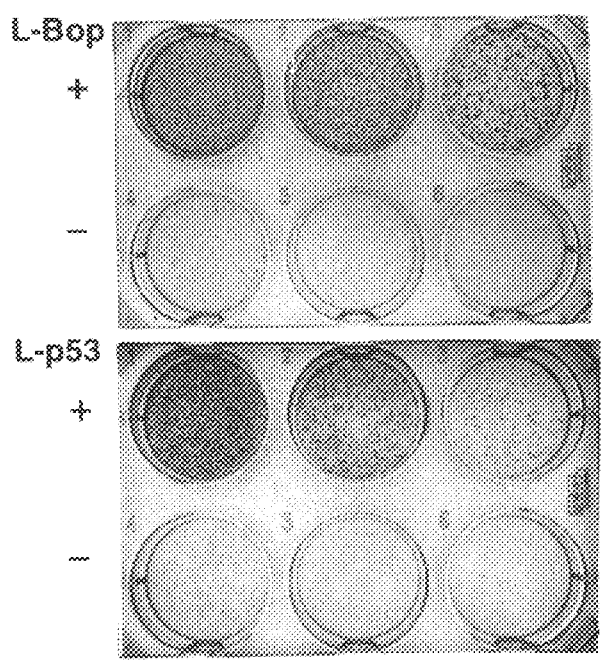
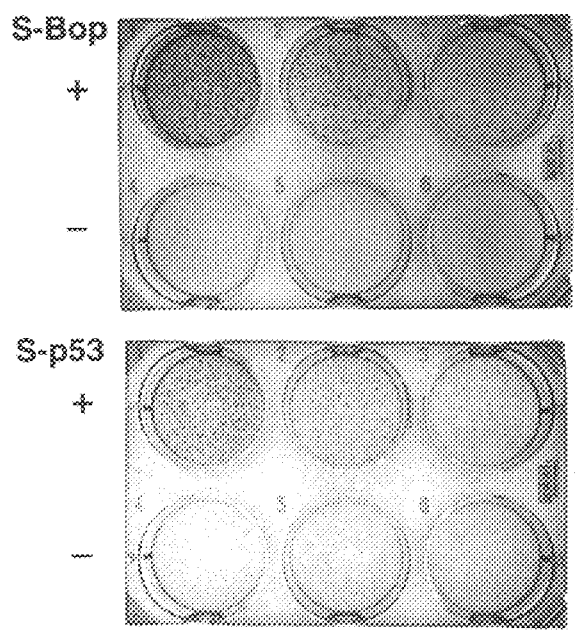
FIG. 3A
FIG. 3B
FIG. 3C
FIG. 3D

FIG. 4B-1
FIG. 4B-2
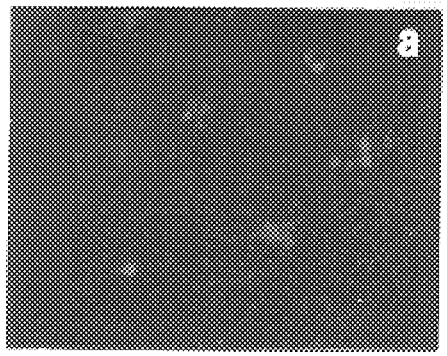
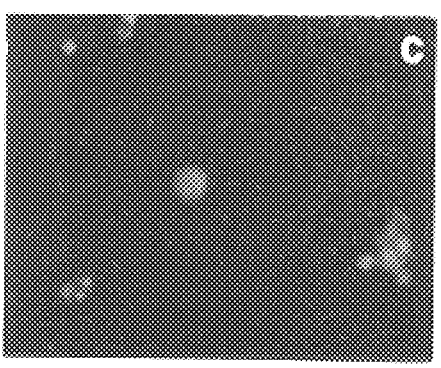
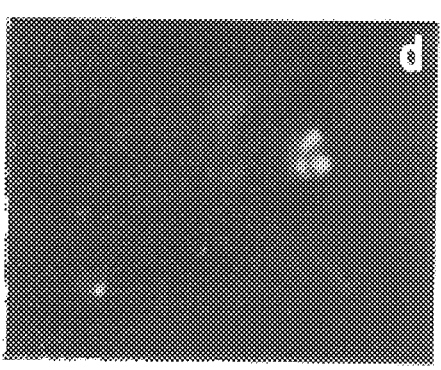
FIG. 4B-3
FIG. 4B-4
FIG. 4C-1
FIG. 4C-2
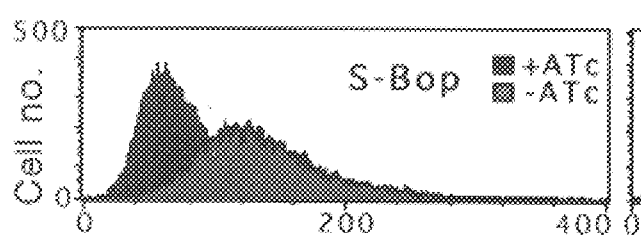
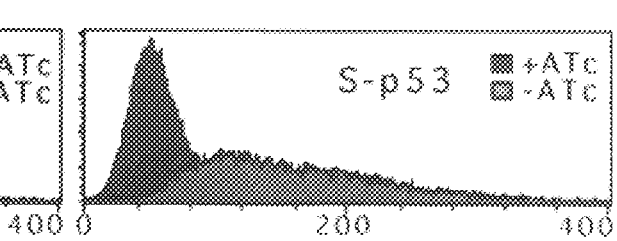
anti-digoxigenin-fluorescein
fluorescence (arbitrary unit)
anti-digoxigenin-fluorescein
fluorescence (arbitrary unit)

FIG. 5A-1
FIG. 5A-2
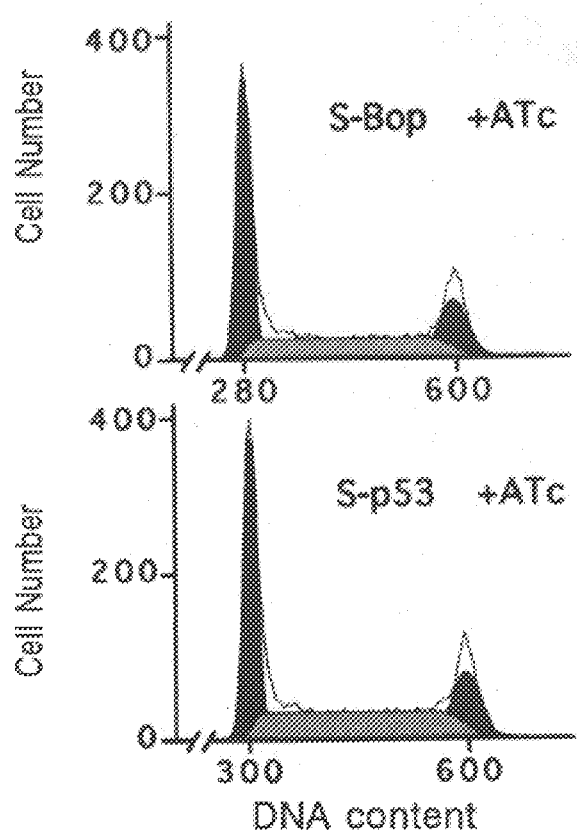
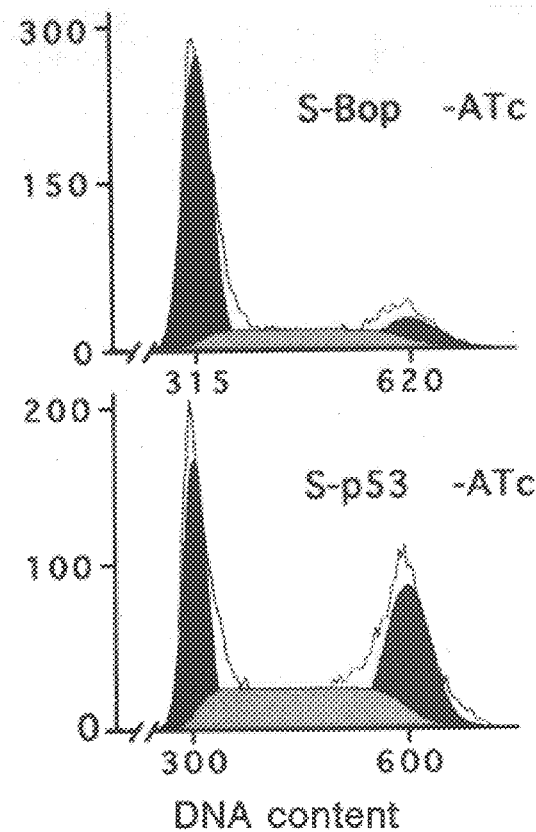
FIG. 5A-3
FIG. 5A-4
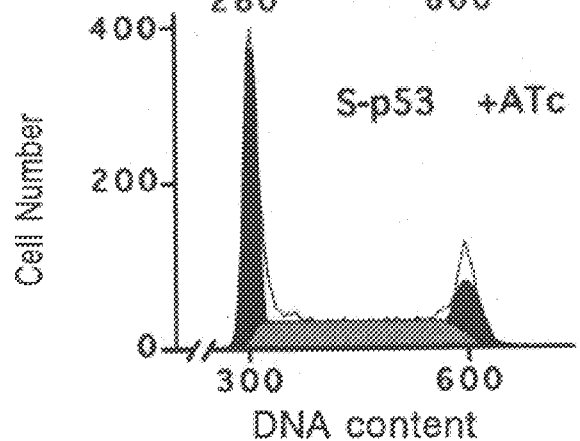
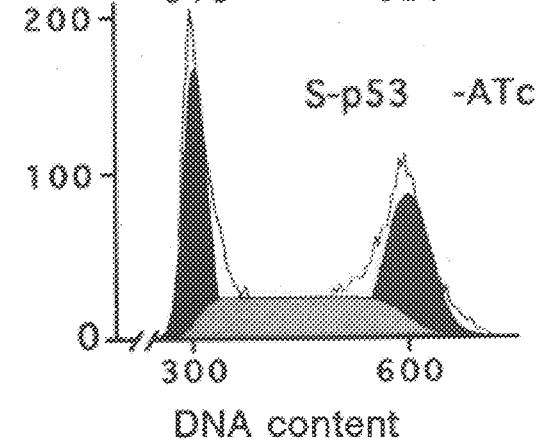
FIG. 5B
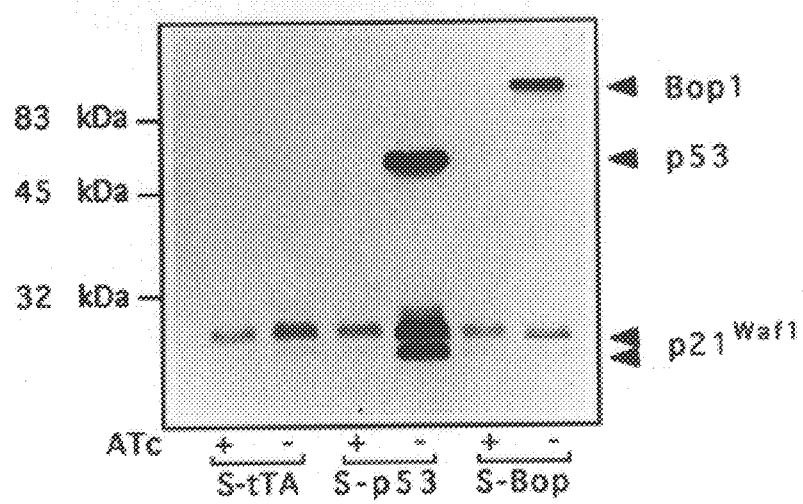

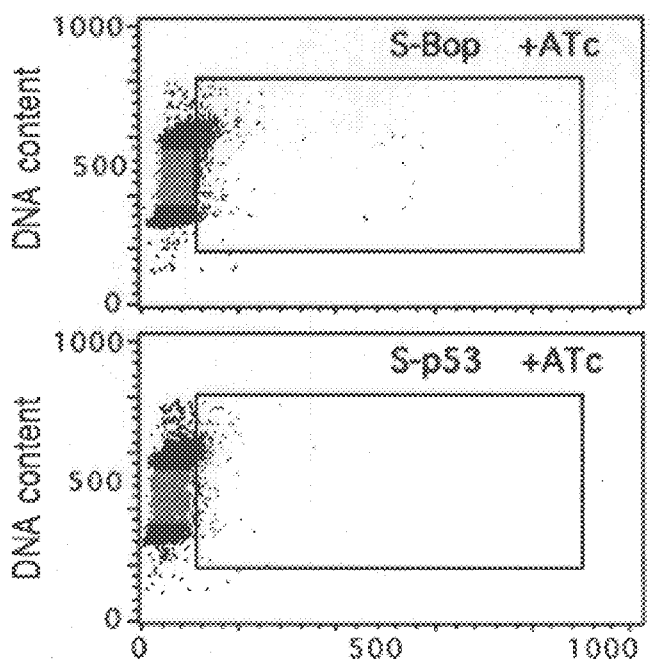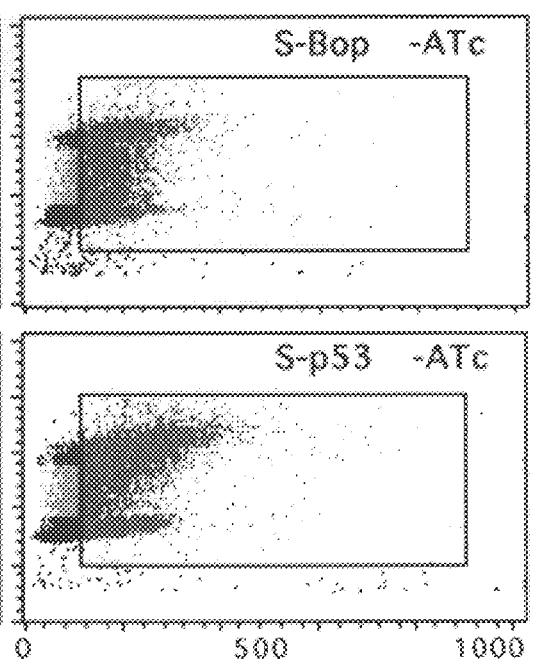
FIG. 5C-1  FIG. 5C-2
FIG. 5C-3  FIG. 5C-4

GB$_Z$M

Bop1/p53

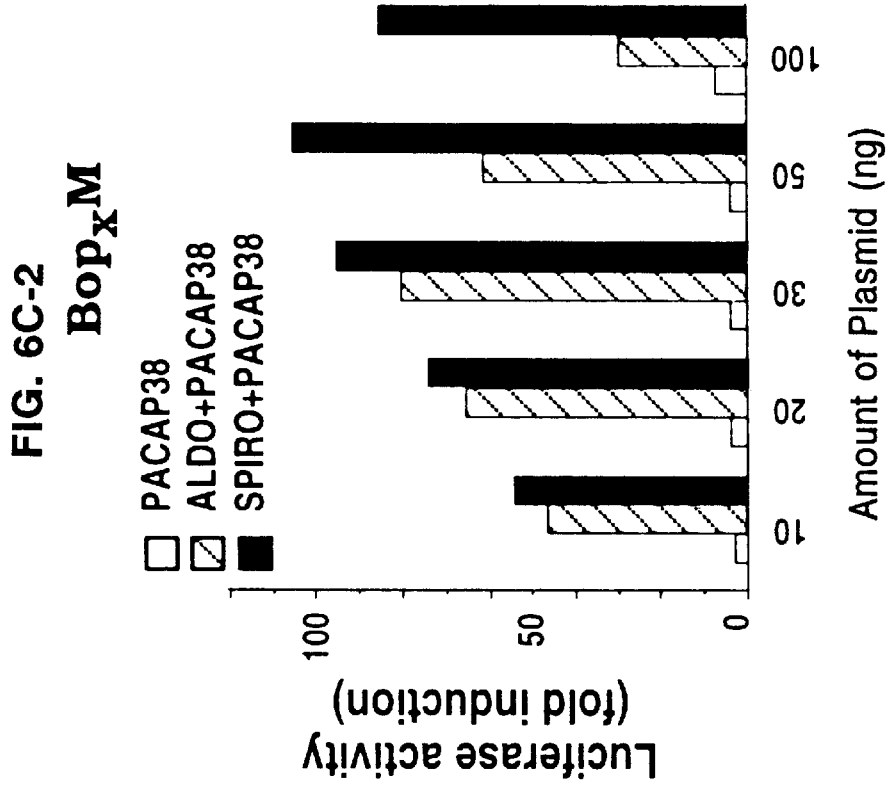
FIG. 6C-1 ΔB$_Z$M
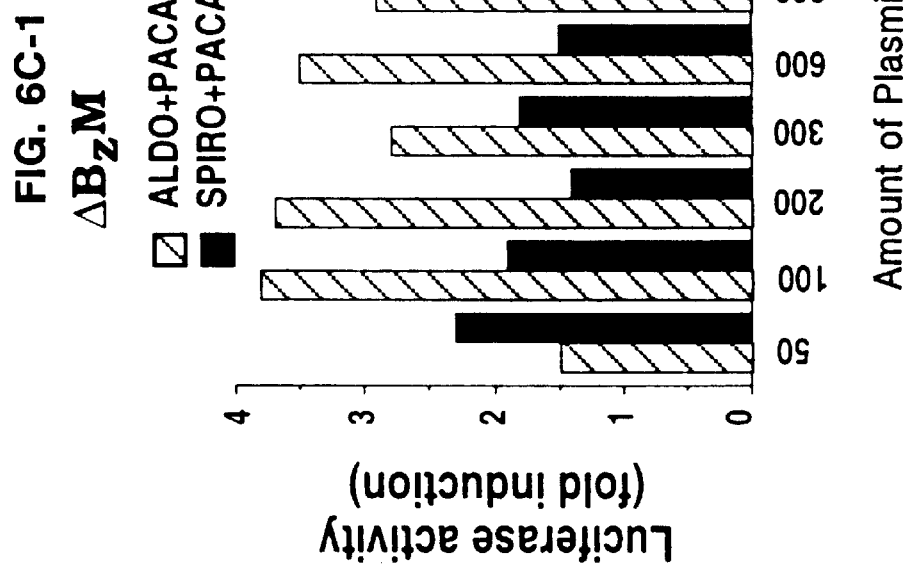
FIG. 6C-2 Bop$_X$M

S-Bop + ATc

S-Bop - ATc

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 2790 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION:542..2545

( x i ) SEQUENCE DESCRIPTION: SEQ ID NO: 1:

```
GAATTCGGGA  GAGCAAGCGG  GCATCTCCTG  GGCGCCGTCA  TGGCTGCTTA  GGCTGCGCTG      60

CCTGCGGATC  GCGGATCCGG  GATCGGAGAT  CTGACGGCGA  CGCCTGAGTC  CGGCTAGGGT     120

AGGTCTGGGT  TGGAGTCTGT  GCCTGCTTCC  TTGGCGTGTG  GTTGTTCCTG  CTTGATTGCT     180

TCAGCGTGCC  ATCGGCTTCG  TATTTGCATA  GGAGTCAGAG  GAGTTAATCT  TGTCTCCTCG     240

AAGATAGACT  CTCATGGTTT  ATGATCCATC  TCTGTGAGAA  GACTTTATTT  GTCTGTCTCT     300

TCTCACAGGT  TTGAGTCTTC  AGACTTCTAC  AGAACTCCAT  AATATCTGCC  TCACAGCTGG     360

CTTTCCTGCT  CTCACAGAAG  ATACCCAGCT  ATTGTGCTCT  GGATCTCTCC  TGGCTGCTAG     420

GCTGTAGCGC  TGCCTTTCTG  GAGTCAGGCT  GTAGTGACTC  CCCACCTTCT  TTCTGTCTGG     480

GCTTAAATGG  CACAGCAGTT  CCTCAGCACA  TCTGAAGAAG  AAAGTGTGAG  AACCAAAGGC     540
```

```
C   ATG  GCT  CCA  TTC  CGC  TGT  CAA  AAA  TGT  GGC  AAG  TCC  TTC  GTC  ACC        586
    Met  Ala  Pro  Phe  Arg  Cys  Gln  Lys  Cys  Gly  Lys  Ser  Phe  Val  Thr
    1              5                        10                       15

CTG  GAG  AAG  TTC  ACC  ATT  CAC  AAT  TAT  TCC  CAC  TCC  AGG  GAG  CGC  CCA        634
Leu  Glu  Lys  Phe  Thr  Ile  His  Asn  Tyr  Ser  His  Ser  Arg  Glu  Arg  Pro
                    20                       25                       30

TTC  AAG  TGC  TCG  AAG  GCT  GAG  TGT  GGC  AAA  GCC  TTC  GTC  TCC  AAG  TAT        682
Phe  Lys  Cys  Ser  Lys  Ala  Glu  Cys  Gly  Lys  Ala  Phe  Val  Ser  Lys  Tyr
                35                       40                       45

AAG  CTG  ATG  AGA  CAC  ATG  GCC  ACA  CAC  TCG  CCA  CAG  AAG  ATT  CAC  CAG        730
Lys  Leu  Met  Arg  His  Met  Ala  Thr  His  Ser  Pro  Gln  Lys  Ile  His  Gln
            50                       55                       60

TGT  ACT  CAC  TGT  GAG  AAG  ACA  TTC  AAC  CGG  AAG  GAC  CAC  CTG  AAG  AAC        778
Cys  Thr  His  Cys  Glu  Lys  Thr  Phe  Asn  Arg  Lys  Asp  His  Leu  Lys  Asn
        65                       70                       75

CAC  CTC  CAG  ACC  CAC  GAT  CCC  AAC  AAG  ATC  TCC  TAC  GCG  TGT  GAC  GAT        826
His  Leu  Gln  Thr  His  Asp  Pro  Asn  Lys  Ile  Ser  Tyr  Ala  Cys  Asp  Asp
    80                       85                       90                       95

TGC  GGC  AAG  AAG  TAC  CAC  ACC  ATG  CTG  GGC  TAC  AAG  AGG  CAC  CTG  GCC        874
Cys  Gly  Lys  Lys  Tyr  His  Thr  Met  Leu  Gly  Tyr  Lys  Arg  His  Leu  Ala
                    100                      105                      110

CTG  CAC  TCG  GCG  AGC  AAT  GGC  GAT  CTC  ACC  TGT  GGG  GTG  TGC  ACC  CTG        922
Leu  His  Ser  Ala  Ser  Asn  Gly  Asp  Leu  Thr  Cys  Gly  Val  Cys  Thr  Leu
                115                      120                      125

GAG  CTG  GGG  AGC  ACC  GAG  GTC  CTG  CTG  GAC  CAC  CTC  AAG  TCT  CAC  GCG        970
Glu  Leu  Gly  Ser  Thr  Glu  Val  Leu  Leu  Asp  His  Leu  Lys  Ser  His  Ala
            130                      135                      140

GAA  GAA  AAG  GCC  AAC  CAG  GCA  CCC  AGG  GAG  AAG  AAA  TAC  CAG  TGC  GAC       1018
Glu  Glu  Lys  Ala  Asn  Gln  Ala  Pro  Arg  Glu  Lys  Lys  Tyr  Gln  Cys  Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 145 |     |     |     |     |     | 150 |     |     |     |     |     | 155 |     |      |
| CAC | TGT | GAT | AGA | TGC | TTC | TAC | ACC | CGG | AAA | GAT | GTG | CGT | CGC | CAC | CTG | 1066 |
| His | Cys | Asp | Arg | Cys | Phe | Tyr | Thr | Arg | Lys | Asp | Val | Arg | Arg | His | Leu |      |
| 160 |     |     |     |     | 165 |     |     |     |     | 170 |     |     |     |     | 175 |      |
| GTG | GTC | CAC | ACA | GGA | TGC | AAG | GAC | TTC | CTG | TGT | CAG | TTC | TGT | GCC | CAG | 1114 |
| Val | Val | His | Thr | Gly | Cys | Lys | Asp | Phe | Leu | Cys | Gln | Phe | Cys | Ala | Gln |      |
|     |     |     |     | 180 |     |     |     |     | 185 |     |     |     |     | 190 |     |      |
| AGA | TTT | GGG | CGC | AAA | GAC | CAC | CTC | ACT | CGT | CAC | ACC | AAG | AAG | ACC | CAC | 1162 |
| Arg | Phe | Gly | Arg | Lys | Asp | His | Leu | Thr | Arg | His | Thr | Lys | Lys | Thr | His |      |
|     |     |     | 195 |     |     |     |     | 200 |     |     |     |     | 205 |     |     |      |
| TCC | CAG | GAG | CTG | ATG | CAA | GAG | AAT | ATG | CAG | GCA | GGA | GAT | TAC | CAG | AGC | 1210 |
| Ser | Gln | Glu | Leu | Met | Gln | Glu | Asn | Met | Gln | Ala | Gly | Asp | Tyr | Gln | Ser |      |
|     |     | 210 |     |     |     |     | 215 |     |     |     |     | 220 |     |     |     |      |
| AAT | TTC | CAA | CTC | ATT | GCG | CCT | TCA | ACT | TCG | TTC | CAG | ATA | AAG | GTT | GAT | 1258 |
| Asn | Phe | Gln | Leu | Ile | Ala | Pro | Ser | Thr | Ser | Phe | Gln | Ile | Lys | Val | Asp |      |
|     | 225 |     |     |     |     | 230 |     |     |     |     | 235 |     |     |     |     |      |
| CCC | ATG | CCT | CCT | TTC | CAG | CTA | GGA | GCG | GCT | CCC | GAG | AAC | GGG | CTT | GAT | 1306 |
| Pro | Met | Pro | Pro | Phe | Gln | Leu | Gly | Ala | Ala | Pro | Glu | Asn | Gly | Leu | Asp |      |
| 240 |     |     |     |     | 245 |     |     |     |     | 250 |     |     |     |     | 255 |      |
| GGT | GGC | TTG | CCA | CCC | GAG | GTT | CAT | GGT | CTA | GTG | CTT | GCT | GCC | CCA | GAA | 1354 |
| Gly | Gly | Leu | Pro | Pro | Glu | Val | His | Gly | Leu | Val | Leu | Ala | Ala | Pro | Glu |      |
|     |     |     |     | 260 |     |     |     |     | 265 |     |     |     |     | 270 |     |      |
| GAA | GCT | CCC | CAA | CCC | ATG | CCG | CCC | TTG | GAG | CCT | TTG | GAG | CCT | TTG | GAG | 1402 |
| Glu | Ala | Pro | Gln | Pro | Met | Pro | Pro | Leu | Glu | Pro | Leu | Glu | Pro | Leu | Glu |      |
|     |     |     | 275 |     |     |     |     | 280 |     |     |     |     | 285 |     |     |      |
| CCT | TTG | GAG | CCT | TTG | GAG | CCG | ATG | CAG | TCT | TTG | GAG | CCT | TTG | CAG | CCT | 1450 |
| Pro | Leu | Glu | Pro | Leu | Glu | Pro | Met | Gln | Ser | Leu | Glu | Pro | Leu | Gln | Pro |      |
|     |     | 290 |     |     |     |     | 295 |     |     |     |     | 300 |     |     |     |      |
| TTG | GAG | CCG | ATG | CAG | CCT | TTG | GAG | CCA | ATG | CAG | CCT | TTG | GAG | CCG | ATG | 1498 |
| Leu | Glu | Pro | Met | Gln | Pro | Leu | Glu | Pro | Met | Gln | Pro | Leu | Glu | Pro | Met |      |
|     | 305 |     |     |     |     | 310 |     |     |     |     | 315 |     |     |     |     |      |
| CAG | CCT | TTA | GAG | CCT | TTG | GAG | CCT | CTG | GAG | CCG | ATG | CAG | CCT | TTG | GAG | 1546 |
| Gln | Pro | Leu | Glu | Pro | Leu | Glu | Pro | Leu | Glu | Pro | Met | Gln | Pro | Leu | Glu |      |
| 320 |     |     |     |     | 325 |     |     |     |     | 330 |     |     |     |     | 335 |      |
| CCG | ATG | CAG | CCT | TTG | GAG | CCT | ATG | CAG | CCA | ATG | CTG | CCA | ATG | CAG | CCA | 1594 |
| Pro | Met | Gln | Pro | Leu | Glu | Pro | Met | Gln | Pro | Met | Leu | Pro | Met | Gln | Pro |      |
|     |     |     | 340 |     |     |     |     | 345 |     |     |     |     | 350 |     |     |      |
| ATG | CAG | CCA | ATG | CAG | CCA | ATG | CAG | CCA | ATG | CTG | CCA | ATG | CAG | CCA | ATG | 1642 |
| Met | Gln | Pro | Met | Gln | Pro | Met | Gln | Pro | Met | Leu | Pro | Met | Gln | Pro | Met |      |
|     | 355 |     |     |     |     | 360 |     |     |     |     | 365 |     |     |     |     |      |
| CTG | CCA | ATG | CAG | CCA | ATG | CAG | CCA | ATG | CAG | CCA | ATG | CTG | CCA | ATG | CCA | 1690 |
| Leu | Pro | Met | Gln | Pro | Met | Gln | Pro | Met | Gln | Pro | Met | Leu | Pro | Met | Pro |      |
| 370 |     |     |     |     | 375 |     |     |     |     | 380 |     |     |     |     |     |      |
| GAG | CCG | TCT | TTC | ACT | CTG | CAC | CCT | GGC | GTA | GTT | CCC | ACC | TCT | CCT | CCC | 1738 |
| Glu | Pro | Ser | Phe | Thr | Leu | His | Pro | Gly | Val | Val | Pro | Thr | Ser | Pro | Pro |      |
|     | 385 |     |     |     |     | 390 |     |     |     |     | 395 |     |     |     |     |      |
| CCA | ATT | ATT | CTT | CAG | GAG | CAT | AAG | TAT | AAT | CCT | GTT | CCT | ACC | TCA | TAT | 1786 |
| Pro | Ile | Ile | Leu | Gln | Glu | His | Lys | Tyr | Asn | Pro | Val | Pro | Thr | Ser | Tyr |      |
| 400 |     |     |     |     | 405 |     |     |     |     | 410 |     |     |     |     | 415 |      |
| GCC | CCA | TTT | GTA | GGC | ATG | CCC | GTC | AAA | GCA | GAT | GGC | AAG | GCC | TTT | TGC | 1834 |
| Ala | Pro | Phe | Val | Gly | Met | Pro | Val | Lys | Ala | Asp | Gly | Lys | Ala | Phe | Cys |      |
|     |     |     |     | 420 |     |     |     |     | 425 |     |     |     |     | 430 |     |      |
| AAC | GTG | GGT | TTC | TTT | GAG | GAA | TTT | CCT | CTG | CAA | GAG | CCT | CAG | GCG | CCT | 1882 |
| Asn | Val | Gly | Phe | Phe | Glu | Glu | Phe | Pro | Leu | Gln | Glu | Pro | Gln | Ala | Pro |      |
|     |     |     | 435 |     |     |     |     | 440 |     |     |     |     | 445 |     |     |      |
| CTC | AAG | TTC | AAC | CCA | TGT | TTT | GAG | ATG | CCT | ATG | GAG | GGG | TTT | GGG | AAA | 1930 |
| Leu | Lys | Phe | Asn | Pro | Cys | Phe | Glu | Met | Pro | Met | Glu | Gly | Phe | Gly | Lys |      |
|     |     | 450 |     |     |     |     | 455 |     |     |     |     | 460 |     |     |     |      |
| GTC | ACC | CTG | TCC | AAA | GAG | CTG | CTG | GTA | GAT | GCT | GTG | AAT | ATA | GCC | ATT | 1978 |
| Val | Thr | Leu | Ser | Lys | Glu | Leu | Leu | Val | Asp | Ala | Val | Asn | Ile | Ala | Ile |      |

| | | | | | | | | | | | | | | | |
|---|---|---|---|---|---|---|---|---|---|---|---|---|---|---|---|
| | | | | 465 | | | | | 470 | | | | | 475 | |
| CCT | GCC | TCT | CTG | GAG | ATT | TCC | TCC | CTA | TTG | GGG | TTT | TGG | CAG | CTC | CCC | 2026
| Pro | Ala | Ser | Leu | Glu | Ile | Ser | Ser | Leu | Leu | Gly | Phe | Trp | Gln | Leu | Pro |
| 480 | | | | | 485 | | | | | 490 | | | | | 495 |
| CCT | CCT | ACT | CCC | CAG | AAT | GGC | TTT | GTG | AAT | AGC | ACC | ATC | CCT | GTG | GGG | 2074
| Pro | Pro | Thr | Pro | Gln | Asn | Gly | Phe | Val | Asn | Ser | Thr | Ile | Pro | Val | Gly |
| | | | | 500 | | | | | 505 | | | | | 510 | |
| CCT | GGG | GAG | CCA | CTG | CCC | CAT | AGG | ATA | ACC | TGT | CTG | GCG | CAG | CAG | CAG | 2122
| Pro | Gly | Glu | Pro | Leu | Pro | His | Arg | Ile | Thr | Cys | Leu | Ala | Gln | Gln | Gln |
| | | | | 515 | | | | | 520 | | | | | 525 | |
| CCA | CCG | CCA | CTG | CCG | CCG | CCA | CCG | CTG | CCA | CTG | CCA | CAG | CCA | CTG | | 2170
| Pro | Pro | Pro | Leu | Pro | Pro | Pro | Pro | Leu | Pro | Leu | Pro | Gln | Pro | Leu | |
| | | 530 | | | | | 535 | | | | | 540 | | | |
| CCA | GTG | CCA | CAG | CCA | CTA | CCA | CAG | CCA | CAG | ATG | CAG | CCA | CAG | TTT | CAG | 2218
| Pro | Val | Pro | Gln | Pro | Leu | Pro | Gln | Pro | Gln | Met | Gln | Pro | Gln | Phe | Gln |
| | 545 | | | | | 550 | | | | | 555 | | | | |
| TTG | CAG | ATC | CAG | CCC | CAG | ATG | CAG | CTA | CCA | CAG | CTG | CTG | CCG | CAA | CTG | 2266
| Leu | Gln | Ile | Gln | Pro | Gln | Met | Gln | Leu | Pro | Gln | Leu | Leu | Pro | Gln | Leu |
| 560 | | | | | 565 | | | | | 570 | | | | | 575 |
| CAA | CCT | CAG | CAG | CAG | CCT | GAT | CCT | GAG | CCA | GAG | CCA | GAG | CCA | GAG | CCA | 2314
| Gln | Pro | Gln | Gln | Gln | Pro | Asp | Pro | Glu | Pro | Glu | Pro | Glu | Pro | Glu | Pro |
| | | | | 580 | | | | | 585 | | | | | 590 | |
| GAG | CCA | GAG | CCA | GAG | CCA | GAG | CCG | GAA | CCG | GAA | CCG | GAG | CCA | GAG | CCA | 2362
| Glu | Pro | Glu | Pro | Glu | Pro | Glu | Pro | Glu | Pro | Glu | Pro | Glu | Pro | Glu | Pro |
| | | | | 595 | | | | | 600 | | | | | 605 | |
| GAG | CCA | GAA | CCA | GAG | CCA | GAG | GAA | GAA | CAG | GAA | GAG | GCA | GAA | GAA | GAG | 2410
| Glu | Pro | Glu | Pro | Glu | Pro | Glu | Glu | Glu | Gln | Glu | Glu | Ala | Glu | Glu | Glu |
| | | 610 | | | | | 615 | | | | | 620 | | | |
| GCA | GAG | GAA | GGA | GCA | GAG | GAA | GGA | GCA | GAA | CCA | GAG | GCA | CAG | GCA | GAA | 2458
| Ala | Glu | Glu | Gly | Ala | Glu | Glu | Gly | Ala | Glu | Pro | Glu | Ala | Gln | Ala | Glu |
| | | 625 | | | | | 630 | | | | | 635 | | | |
| GAA | GAG | GAA | GAG | GAA | GAG | GAA | GCG | GAA | GAG | CCA | CAG | CCA | GAA | GAA | GCC | 2506
| Glu | Glu | Glu | Glu | Glu | Glu | Glu | Ala | Glu | Glu | Pro | Gln | Pro | Glu | Glu | Ala |
| 640 | | | | | 645 | | | | | 650 | | | | | 655 |
| CAA | ATA | GCA | GGA | CTC | GTC | TAT | AAG | AAA | TGG | ACA | GTT | TAG | TTCCTCTTCT | | | 2555
| Gln | Ile | Ala | Gly | Leu | Val | Tyr | Lys | Lys | Trp | Thr | Val | * | | | |
| | | | | 660 | | | | | 665 | | | | | | |

TGTTAGCTTA CTCTGTAGTT TCTTCTTCTT GTTGCCCATT GTGTAGCTTT ATAGAGTGTG 2615

ACGCTATTGA TGTCTCCATT TTTTAAAGTG AATTTAAATG TACTGTTCAA TATTTTTCAT 2675

GTGATGTTGT TCCAATGTGA GTTACGACTT CATTTATCTT AAAGACAAAA CTGGTTGTCA 2735

GTCATATCTG ACAGAAGAAA GAAATCACTG TGTAACCAAG CCATATAGCG GCCGC 2790

( 2 ) INFORMATION FOR SEQ ID NO: 2:

( i ) SEQUENCE CHARACTERISTICS:
        ( A ) LENGTH: 667 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Ala | Pro | Phe | Arg | Cys | Gln | Lys | Cys | Gly | Lys | Ser | Phe | Val | Thr | Leu |
| 1 | | | | 5 | | | | | 10 | | | | | 15 | |
| Glu | Lys | Phe | Thr | Ile | His | Asn | Tyr | Ser | His | Ser | Arg | Glu | Arg | Pro | Phe |
| | | | 20 | | | | | 25 | | | | | 30 | | |
| Lys | Cys | Ser | Lys | Ala | Glu | Cys | Gly | Lys | Ala | Phe | Val | Ser | Lys | Tyr | Lys |
| | | | 35 | | | | | 40 | | | | | 45 | | |
| Leu | Met | Arg | His | Met | Ala | Thr | His | Ser | Pro | Gln | Lys | Ile | His | Gln | Cys |

```
                50                          55                          60
Thr His Cys Glu Lys Thr Phe Asn Arg Lys Asp His Leu Lys Asn His
 65                      70                      75                      80

Leu Gln Thr His Asp Pro Asn Lys Ile Ser Tyr Ala Cys Asp Asp Cys
                     85                      90                      95

Gly Lys Lys Tyr His Thr Met Leu Gly Tyr Lys Arg His Leu Ala Leu
                100                     105                     110

His Ser Ala Ser Asn Gly Asp Leu Thr Cys Gly Val Cys Thr Leu Glu
                115                     120                     125

Leu Gly Ser Thr Glu Val Leu Leu Asp His Leu Lys Ser His Ala Glu
        130                     135                     140

Glu Lys Ala Asn Gln Ala Pro Arg Glu Lys Lys Tyr Gln Cys Asp His
145                     150                     155                     160

Cys Asp Arg Cys Phe Tyr Thr Arg Lys Asp Val Arg Arg His Leu Val
                165                     170                     175

Val His Thr Gly Cys Lys Asp Phe Leu Cys Gln Phe Cys Ala Gln Arg
                180                     185                     190

Phe Gly Arg Lys Asp His Leu Thr Arg His Thr Lys Lys Thr His Ser
            195                     200                     205

Gln Glu Leu Met Gln Glu Asn Met Gln Ala Gly Asp Tyr Gln Ser Asn
    210                     215                     220

Phe Gln Leu Ile Ala Pro Ser Thr Ser Phe Gln Ile Lys Val Asp Pro
225                     230                     235                     240

Met Pro Pro Phe Gln Leu Gly Ala Ala Pro Glu Asn Gly Leu Asp Gly
                245                     250                     255

Gly Leu Pro Pro Glu Val His Gly Leu Val Leu Ala Ala Pro Glu Glu
                260                     265                     270

Ala Pro Gln Pro Met Pro Pro Leu Glu Pro Leu Glu Pro Leu Glu Pro
            275                     280                     285

Leu Glu Pro Leu Glu Pro Met Gln Ser Leu Glu Pro Leu Gln Pro Leu
        290                     295                     300

Glu Pro Met Gln Pro Leu Glu Pro Met Gln Pro Leu Glu Pro Met Gln
305                     310                     315                     320

Pro Leu Glu Pro Leu Glu Pro Leu Glu Pro Met Gln Pro Leu Glu Pro
                325                     330                     335

Met Gln Pro Leu Glu Pro Met Gln Pro Met Leu Pro Met Gln Pro Met
                340                     345                     350

Gln Pro Met Gln Pro Met Gln Pro Met Leu Pro Met Gln Pro Met Leu
            355                     360                     365

Pro Met Gln Pro Met Gln Pro Met Gln Pro Met Leu Pro Met Pro Glu
        370                     375                     380

Pro Ser Phe Thr Leu His Pro Gly Val Val Pro Thr Ser Pro Pro Pro
385                     390                     395                     400

Ile Ile Leu Gln Glu His Lys Tyr Asn Pro Val Pro Thr Ser Tyr Ala
                405                     410                     415

Pro Phe Val Gly Met Pro Val Lys Ala Asp Gly Lys Ala Phe Cys Asn
                420                     425                     430

Val Gly Phe Phe Glu Glu Phe Pro Leu Gln Glu Pro Gln Ala Pro Leu
            435                     440                     445

Lys Phe Asn Pro Cys Phe Glu Met Pro Met Glu Gly Phe Gly Lys Val
    450                     455                     460

Thr Leu Ser Lys Glu Leu Leu Val Asp Ala Val Asn Ile Ala Ile Pro
465                     470                     475                     480
```

```
Ala  Ser  Leu  Glu  Ile  Ser  Ser  Leu  Leu  Gly  Phe  Trp  Gln  Leu  Pro  Pro
               485                      490                     495

Pro  Thr  Pro  Gln  Asn  Gly  Phe  Val  Asn  Ser  Thr  Ile  Pro  Val  Gly  Pro
               500                      505                     510

Gly  Glu  Pro  Leu  Pro  His  Arg  Ile  Thr  Cys  Leu  Ala  Gln  Gln  Pro
               515                      520                     525

Pro  Pro  Leu  Pro  Pro  Pro  Pro  Leu  Pro  Leu  Pro  Gln  Pro  Leu  Pro
     530                      535                     540

Val  Pro  Gln  Pro  Leu  Pro  Gln  Pro  Gln  Met  Gln  Pro  Gln  Phe  Gln  Leu
545                      550                     555                          560

Gln  Ile  Gln  Pro  Gln  Met  Gln  Leu  Pro  Gln  Leu  Leu  Pro  Gln  Leu  Gln
                    565                     570                          575

Pro  Gln  Gln  Gln  Pro  Asp  Pro  Glu  Pro  Glu  Pro  Glu  Pro  Glu  Pro  Glu
               580                      585                     590

Pro  Glu  Pro  Glu  Pro  Glu  Pro  Glu  Pro  Glu  Pro  Glu  Pro  Glu  Pro  Glu
          595                      600                     605

Pro  Glu  Pro  Glu  Pro  Glu  Glu  Glu  Gln  Glu  Glu  Ala  Glu  Glu  Glu  Ala
     610                      615                     620

Glu  Glu  Gly  Ala  Glu  Glu  Gly  Ala  Glu  Pro  Glu  Ala  Gln  Ala  Glu  Glu
625                      630                     635                          640

Glu  Glu  Glu  Glu  Glu  Glu  Ala  Glu  Glu  Pro  Gln  Pro  Glu  Glu  Ala  Gln
                    645                     650                          655

Ile  Ala  Gly  Leu  Val  Tyr  Lys  Lys  Trp  Thr  Val
               660                      665
```

( 2 ) INFORMATION FOR SEQ ID NO: 3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO: 3:

```
ATGTCTCGAG  GCCTTTGCGG  CCGCTATANN  NNNNNN                                    36
```

( 2 ) INFORMATION FOR SEQ ID NO: 4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i i ) HYPOTHETICAL: YES ( x i ) SEQUENCE DESCRIPTION: SEQ ID NO: 4:

```
AGGCCATGG                                                                      9
```

( 2 ) INFORMATION FOR SEQ ID NO: 5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i i ) HYPOTHETICAL: YES ( i x ) FEATURE:
        ( A ) NAME/KEY: -

(B) LOCATION:3
(D) OTHER INFORMATION:/note= "N at position 3 is A or G."

(x i) SEQUENCE DESCRIPTION: SEQ ID NO: 5:

CCNCCATGG                                                                                              9

(2) INFORMATION FOR SEQ ID NO: 6:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i i) HYPOTHETICAL: YES (x i) SEQUENCE DESCRIPTION: SEQ ID NO: 6:

His  Ser  Arg  Glu  Arg  Pro  Phe  Lys  Cys
      1                        5

(2) INFORMATION FOR SEQ ID NO: 7:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i i) HYPOTHETICAL: YES (i x) FEATURE:
      (A) NAME/KEY: Cross-links
      (B) LOCATION:2
      (D) OTHER INFORMATION:/note= "X at position 2 is S or T."

(i x) FEATURE:
      (A) NAME/KEY: Cross-links
      (B) LOCATION:7
      (D) OTHER INFORMATION:/note= "X at position 7 is F or Y."

(x i) SEQUENCE DESCRIPTION: SEQ ID NO: 7:

His  Xaa  Gly  Glu  Lys  Pro  Xaa  Xaa  Cys
      1                        5

(2) INFORMATION FOR SEQ ID NO: 8:

(i) SEQUENCE CHARACTERISTICS:
      (A) LENGTH: 5 amino acids
      (B) TYPE: amino acid
      (C) STRANDEDNESS: single
      (D) TOPOLOGY: linear (i i i) HYPOTHETICAL: YES (x i) SEQUENCE DESCRIPTION: SEQ ID NO: 8:

His  Ser  Pro  Gln  Lys
      1                        5

(2) INFORMATION FOR SEQ ID NO: 9:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i i) HYPOTHETICAL: YES (x i) SEQUENCE DESCRIPTION: SEQ ID NO: 9:

Lys  Lys  Trp  Thr
      1

( 2 ) INFORMATION FOR SEQ ID NO: 10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotid"

( x i ) SEQUENCE DESCRIPTION: SEQ ID NO: 10:

GTGATGGCGG CCGCCATTCC GCTGTCAAAA ATGTG 35

( 2 ) INFORMATION FOR SEQ ID NO: 11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO: 11:

CCGCGCCTCG AGGGTCTTCT TGGTGTGACG 30

( 2 ) INFORMATION FOR SEQ ID NO: 12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO: 12:

GCGGCCGCAG AGCCGTCTTT CACTC 25

( 2 ) INFORMATION FOR SEQ ID NO: 13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO: 13:

CCGCGCCTCG AGAACTGTCC ATTTCTTATA GAC 33

( 2 ) INFORMATION FOR SEQ ID NO: 14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

ATAGCAGTGA GTGCTGTG 18

( 2 ) INFORMATION FOR SEQ ID NO: 15:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO: 15:

GTTTCTTTTC AGGGACTC    18

NUCLEIC ACID MOLECULES CODING FOR TUMOR SUPPRESSOR PROTEINS AND METHODS FOR THEIR ISOLATION

INTRODUCTION

The present invention relates to novel nucleic acid molecules coding for a protein having the biological activity of a tumor suppressor protein. The present invention also provides methods for the isolation of nucleic acid molecules encoding tumor suppressor proteins as well as nucleic acid molecules obtainable by said method. Further, the invention provides vectors comprising said nucleic acid molecules wherein the nucleic acid molecules are operatively linked to regulatory elements allowing expression in prokaryotic or eukaryotic host cells as well as polypeptides encoded by said nucleic acid molecules which have tumor suppressor activity and methods for their production. The present invention further relates to pharmaceutical and diagnostic compositions comprising the aforementioned nucleic acid molecules and/or comprising a nucleic acid molecule which is complementary to such a nucleic acid molecule. Described are also compositions which comprise polypeptides encoded by the described nucleic acid molecules which have tumor suppressor activity and/or an antibody specifically recognizing such polypeptides.

BACKGROUND OF THE INVENTION

A network of genes, including cell cycle regulatory genes, proto-oncogenes, and tumor suppressor genes have emerged, which play major roles in normal physiological processes as well as in tumor progression (Grana and Reddy, Oncogene 11 (1995), 221–219; Hartwell and Kastan, Science 266 (1994), 1821–1828; Hoffman and Liebermann, Oncogene 9 (1995), 1807–1812; Sherr, Cell 79 (1994), 551–555). Oncogenes have first captured the lion's share of attention in the molecular and genetic studies on cell transformation. But it has now been realized that there is an equally important second side of the coin, presented by a distinct class of genes known variously as tumor suppressor genes (TSGs) or anti-oncogenes. Logic dictates that there must exist an equally elaborate array of growth-constraining elements in the cell's signaling circuitry that serve to counteract the growth-promoting proto-oncogenes (Fisher, Cell 78 (1994), 539–542; Karp and Broder, Nature Med. 1 (1995), 309–320; Liebermann et al., Oncogene 11 (1995), 119–210; Thompson, Science 267 (1995), 1456–1462). These tumor suppressor genes are of special interest since they may open up new possibilities for the treatment of cancers of various kinds and may help to better understand the molecular mechanisms responsible for the development of cancer.

The isolation of such suppressor genes has become feasible by progress in various fields with major contributions of molecular genetics and cell cycle analysis. Molecular genetics applied linkage studies to the isolation of TSGs, but the most fruitful strategies have evolved from the study of the genetic mechanisms employed by nascent tumor cells to discard their second, surviving copy of a tumor suppressor gene which results in homozygosity at the tumor suppressor locus. This event can often be traced by following the fate of anonymous DNA markers whose polymorphism allows detection of hetero- and homozygous states in these chromosomal regions. By this strategy the identification of the retinoblastoma gene product (Rb), the Wilms tumor suppressor gene (WT) and the von Hippel-Lindau tumor-suppressor gene has been possible. Most recently the cloning of the breast cancer susceptibility genes, BRCA1 and BRCA2 (Miki et al., Science 266 (1995), 66–71; Wooster et al., Nature 378 (1995), 789–792) has been accomplished by this approach.

Yet, the vast majority of human cancers, including breast cancer, develop spontaneously or under poorly defined criteria of genetic susceptibility preventing linkage studies to perform and indicating that epigenetic mechanisms appear to play the major role in the initiation and formation of tumors, which seem to develop in a multi-step process.

Further support for the concept of TSGs came up with the characterization and isolation of the regulatory components of the mammalian cell cycle. This progress has led to the identification of a new class of candidate tumor suppressor genes, the ubiquitously expressed cyclin-dependent kinase inhibitors (cdk), which negatively regulate cell cycle progression. Among the various forms described so far (p15, p16, p18, p21 and p27) the cdk p16 has been demonstrated to be mutated in-vivo in a spectrum of tumors examined (Marx, Science 264 (1994), 344–345; Kamb et al., Science 264 (1994), 436–440; Nobori et al., Nature 368 (1994), 753–756).

Another important example of a tumor suppressor gene is the p53 TSG, whose biological activity has been elucidated in-vitro through molecular and biochemical studies before it became identified as the genetic cause of the Li-Fraumeni syndrome. It is one of the most frequently mutated tumor suppressor genes in human tumors from various origins (Hollstein et al., Science 253 (1991), 49–53). This TSG encodes a transcription factor with two important functional properties contributing to its growth-suppression function: induction of apoptosis and cell cycle arrest (Vogelstein and Kinzler, Cell 70 (1992), 523–526; Oren, FASEB J. 6 (1992), 3169–3176; Perry, Curr. Opin. Genet. Dev. 3 (1993), 50–54; Bates and Vousden, Curr. Opin. Genet. Dev. 6 (1996), 12–19).

Although tumor suppressor genes have recently attracted a lot of attention due to the possibility that they may provide important targets in the treatment of cancer, only a limited number of TSGs could be identified and cloned. Thus, there still exists a need for the identification of further tumor suppressor genes in order to better understand the mechanisms of the development of diseases such as cancer and to be able to provide means for the treatment of further forms of tumorous diseases or for the improved treatment of tumorous diseases. One reason for the slow progress in cloning TSGs may be seen in the fact that there exists no method for the identification and isolation which can be easily carried out in-vitro and allows the rapid screening of a plurality of potential sequences for tumor suppressor activity.

Thus, the technical problem underlying the present invention is to provide further nucleic acid molecules coding for proteins displaying tumor suppressor activity as well as methods for their identification and isolation.

DESCRIPTION OF THE INVENTION

The solution to the above technical problem is achieved by providing the embodiments characterized in the claims. Namely, nucleic acid molecules coding for a novel class of tumor suppressor proteins have been identified. This has been achieved by using an in-vitro functional expression transductory cloning technique. The described novel class of tumor suppressor proteins shares the ability of p53 to inhibit growth of tumor cells by controlling apoptotic cell death and cell cycle progression and appears to play a critical role in apoptosis and cell cycle regulation. However, the newly identified tumor suppressors display a restricted pattern of tissue expression and distinct activities compared to known TSGs such as p53.

Thus, in one aspect, the present invention relates to a nucleic acid molecule encoding a protein having the biological activity of a tumor suppressor selected from the group consisting of:

(a) nucleic acid molecules coding for a polypeptide comprising the amino acid sequence given in SEQ ID NO.2;

(b) nucleic acid molecules comprising the nucleotide sequence given in SEQ ID NO.1;

(c) nucleic acid molecules hybridizing to a nucleic acid molecule as defined in (a) or (b); and (d) nucleic acid molecules, the nucleotide sequence of which is degenerate as a result of the genetic code to a nucleotide sequence of a nucleic acid molecule as defined in (a), (b) or (c).

The nucleic acid molecule with the nucleotide sequence of the coding region as depicted in SEQ ID NO. 1 codes for a protein of 667 amino acids with a predicted molecular weight of 75 kDa (FIG. 1A). The ATG of AGGCC<u>ATG</u>G (SEQ ID NO. 4) was assigned as initiation codon on the basis of its close match to the CC(A/G)CCATGG (SEQ ID NO. 5) Kozak consensus sequence for favored initiation of translation and the presence of an in-frame TGA stop codon 12 nucleotides upstream. Data base searches revealed the presence of seven zinc fingers (Klug and Schwabe, FASEB J. (1995), 597–604) in the N-terminal region. However, homologies to other members of the zinc finger protein family were low (30% for the best), with the closest group being the GLI-Krüppel family of zinc finger proteins which have been implicated in normal development and tumor formation (Ruppert et al., Mol. Cell. Biol. 8 (1988), 3104–3113). In particular, the first H/C link (HSRERPFKC (SEQ ID NO. 6)) is in good agreement with the consensus motif for the GLI-Krüppel family (H(S/T)GEKP(F/Y)XC (SEQ ID NO. 7)) (Schuh et al., Cell 47 (1986), 1025–1032). On the other hand, the remaining 459 C-terminal amino acids displayed no significant homologies to sequences in the Swissprot and NBRF-PIR data bases. The central region of the protein (275–383) is characterized by 34 PLE, PMQ or PML repeats, suggestive of a structure known as poly proline type II helix which is considered to be critically involved in protein-protein interactions (Williamson, Biochem. J. 297 (1994), 249–260). The COOH-terminal region is particularly P-, Q- and E-rich, a feature often displayed by transactivation domains of transcription factors. In addition, the presence of a putative phosphorylation site (H<u>S</u>PQK (SEQ ID NO. 8)) for cyclin-dependent kinases (Cdks) located between the second and third zinc finger motif (residues 56–60) as well as a putative protein kinase A (PKA)-phosphorylation site (KKW<u>T</u> (SEQ ID NO. 9)) at the very C-terminus (residues 663–666) suggests possible regulation by protein kinases.

Studies which had been carried out in the scope of the present invention revealed that the protein encoded by the nucleic acid sequence of SEQ ID NO. 1 displays the biological activity of a tumor suppressor.

The term "tumor suppressor", as used herein, relates to any protein/polypeptide inhibiting growth of tumor cells in-vitro and/or in-vivo. Growth inhibition involves mechanisms such as control of apoptosis and/or of cell cycle progression as well as mechanisms unidentified so far. "Tumor suppressors" are proteins displaying biological activities identical to or similar to those of p53, Rb (retinoblastoma gene product), WT (Wilms tumor suppressor gene), VHL (von Hippel-Lindau tumor suppressor gene), BRCA1 (breast cancer susceptibility gene) and p16 (cyclin-dependent kinase inhibitor).

Examples for important biological activities of a tumor suppressor are the capability to inhibit in-vitro proliferation of tumor cells as evidenced for instance by measuring colony formation, growth rate and cloning in soft agar as well as the capability to inhibit in-vivo tumor formation in nude mice. These biological activities can be determined, for example, according to Zhou et al., Proc. Natl. Acad. Sci. USA 91 (1994), 4165–4169; Chen et al., Science 250 (1990), 1576–1580; Baker et al., Science 249 (1990), 912–915; Diller et al., Mol. Cell. Biol. 10 (1990), 5772–5781; Casey et al., Oncogene 6 (1991), 1791–1797; Cheng et al., Cancer Research (1992), 222–226; Wang and Prives, Nature 376 (1995), 88–91; Mercer et al., Proc. Natl. Acad. Sci. USA 87 (1990), 6166–6170; Antelman et al., Oncogene 10 (1995), 697–704.

The protein encoded by the nucleic acid sequence of SEQ ID NO. 1 displays the ability to suppress tumor cell proliferation which could be demonstrated by the constitutive and induced expression of said protein in transfected tumor cells. Furthermore, said protein is capable of inhibiting anchorage-independent growth which is often correlated with tumorigenesis and is a strong criteria for cultured cell transformation. Furthermore, this novel protein is able to suppress tumor formation of transformed cells injected in nude mice. Thus, the protein of the invention displays all essential features of a tumor suppressor similar to those of, for example, p53. This new tumor suppressor is also able to induce apoptosis resulting in inhibition of tumor cell growth. However, this new tumor suppressor exhibits functional differences compared to p53, for instance the induction of apoptotic cell death is more pronounced in Saos-2 cells for the protein of the invention than for p53. Furthermore, the tumor suppressor of the invention induces G1 arrest of the cell cycle, in contrast to p53, independently from the transactivation of the gene encoding the cyclin-dependent kinase inhibitor p21. Finally, it had been shown that this protein acts as nuclear transcription factor.

From the above it is evident that the nucleotide sequence depicted in SEQ ID NO. 1 codes for a novel class of tumor suppressors. By the provision of this nucleotide sequence it is now possible to isolate identical or similar nucleic acid molecules which code for proteins with the biological activity of a tumor suppressor from other species or organisms. Well-established approaches for the identification and isolation of such related sequences are, for example, the isolation from genomic or cDNA libraries using the complete or part of the disclosed sequence as a probe or the amplification of corresponding nucleic acid molecules by polymerase chain reaction using specific primers.

Thus, the invention also relates to nucleic acid molecules which hybridize to the above described nucleic acid molecules and differ at one or more positions in comparison to these as long as they encode a protein having tumor suppressor activity. Such molecules comprise those which are changed, for example, by deletion(s), insertion(s), alteration (s) or any other modification known in the art in comparison to the above described nucleic acid molecules. Methods for introducing such modifications in the nucleic acid molecules according to the invention are well-known to the person skilled in the art. The invention also relates to nucleic acid molecules the sequence of which differs from the sequence of any of the above-described molecules due to the degeneracy of the genetic code.

With respect to the sequences characterized under (c) above, the term "hybridizing" in this context is understood as referring to conventional hybridization conditions, preferably such as hybridization in 50% formamide/6×SSC/ 0.1% SDS/100 µg/ml ssDNA, in which temperatures for hybridization are above 37° C. and temperatures for washing in 0.1×SSC/0.1% SDS are above 55° C. Most preferably, the term "hybridizing" refers to stringent hybridization conditions.

Nucleic acid molecules which hybridize to molecules according to the invention and encode a tumor suppressor may, for example, be those which code for proteins in which putative phosphorylation sites are altered. Biochemical analysis of the regulation of wild-type p53 sequence-specific DNA binding has, for instance, shown that the unphosphorylated tetramer has a cryptic sequence-specific DNA binding activity. This cryptic or latent state of p53 depends upon a C-terminal negative regulatory domain, which locks the unphosphorylated tetramer in an inactive state. Phosphorylation of the C-terminal negative regulatory domain of latent p53 by either protein kinase C or casein kinase II or deletion of the regulatory domain activates sequence-specific DNA binding. In addition, a monoclonal antibody can mimic the effects of protein kinases and activate latent p53. Thus, neutralization of this negative regulatory domain by covalent or non-covalent modification is an important stage in the activation of p53. As described above, the protein encoded by SEQ ID NO. 1 has two putative phosphorylation sites for protein kinases. A consensus motive for cyclin-dependent kinases is located in the DNA-binding domain raising the possibility that the DNA-binding affinity can be finetuned by the driving forces of the cell cycle, constituting a putative feedback loop. This regulatory site could offer the interesting possibility that molecular tools directed against cyclin/cyclin-dependent kinase can via this loop modify the activity of this protein and implement apoptosis proficiency to target tissues. Similarly the presence of a motif for protein kinase A at the very C-terminus of the protein transactivations domain could be a critical target to modulate transactivation potency.

The above-described nucleic acid molecules which encode a novel class of tumor suppressors had been identified by using an in-vitro functional transductory cloning technique. Thus, in another aspect, the present invention relates to a process for the identification and cloning of nucleic acid molecules encoding a protein having the biological activity of a tumor suppressor comprising the steps of:

(i) transfecting mammalian cells with
   (a) a first vector comprising a scorable reporter gene operatively linked to regulatory elements comprising at least one cAMP responsive element so located relative to said reporter gene to permit cAMP inducible expression thereof; and
   (b) pools of expression vectors comprising nucleic acid molecules linked to regulatory elements allowing expression in the mammalian cells;
(ii) cultivating the transfected cells under conditions which permit expression of the nucleic acid molecules present in the vectors;
(iii) identifying those vector pools which lead after transfection to expression of said reporter gene in the mammalian cells;
(iv) optionally subdividing the vector pool(s) identified in step (iii) and repeating step (i) to (iii); and
(v) isolating from the so-identified vector pool(s) the nucleic acid molecule present in the vector(s) and testing its product for tumor suppressor activity.

This novel functional expression cloning technique relies on the transcriptional induction of a gene coding for a G-protein coupled receptor (GPCR) which in its activated form stimulates the cAMP signaling pathway which in turn results in the induction of cAMP responsive genes.

In the method of the invention said transcriptional induction of GPCR genes is conferred by the expression of a functional tumor suppressor, the presence of which is detected by subsequent activation of the endogenous signal transduction pathway and can be monitored by activation of a downstream amplificator, for example, a cAMP responsive reporter gene. The GPCR the expression of which is induced by the tumor suppressor may be any GPCR which is active under the culture conditions employed, in the sense that it activates the cAMP signaling pathway. For example, the GPCR may be constitutively active or activated by a cognated ligand. Examples for GPCR which are positively coupled to cAMP production are the calcitonin, parathyroid hormone, thyrotropin, β-adregenic and pituitary adenylate cyclase activating peptide (PACAP) receptors. One may specifically target a tumor suppressor which induces the transcription of a certain GPCR by adding a ligand or a certain combination of different ligands which activate the cognate GPCR the expression of which is induced by the tumor suppressor. In a preferred embodiment the ligand is the peptide PACAP and the GCPR is the PACAP-type 1 (PVR1) receptor (Spengler et al., Nature 365 (1993), 170–175).

As mentioned above, the GPCR may not require to be activated by the addition of a ligand. These may be a, for example, naturally occurring constitutive active native or mutated GPCR.

Regulation of PVR1-receptor expression depends on activation of the endogenous gene by mechanisms at present not known. Delineation of this molecular pathway could allow to determine the cis-regulatory sequences in the PVR-1 receptor used for transactivation by TSGs. Therefore fusion of such a TSG-responsive region to a reporter gene could present an alternative usage of the present method.

Cells which are suitable for the purpose of the described method are such cells which reveal to elevations of intracellular cAMP a nuclear response leading to transcriptional activation of genes linked to a cAMP-responsive element.

Examples for such cells are those of cell line porcine renal epithelial LLC-PK1 (ATCC CC101) and human osteosarcoma Saos-2 (ATCC HTB 85). A suitable cell line is characterized by the presence of a cAMP dependent protein kinase A (PKA) and a cAMP response element (CRE)-binding protein which mediate the effects of cAMP. After binding of cAMP PKA is activated and able to phosphorylate the CRE-binding protein which is activated to turn on the transcription of cAMP responsive genes, namely genes which contain a short regulatory sequence called CRE which provide for binding of the CRE-binding protein; for a general review of the cAMP signaling pathway; see, for example, Alberts et al., Molecular Biology of the Cell, 3rd ed. Garland Publ., Inc. N.Y. (1994) Chapter 15.

Other suitable cell lines may be identified by the person skilled in the art by screening a panel of cell lines for efficient expression of the expression vector employed combined with high transfection efficiency and with high responsiveness to cAMP. Expression and transfection efficiency may be optimized by conventional methods known in the art. Responsiveness to cAMP can be determined, for example, by transfection of a plasmid encoding and expressing a receptor which is positively coupled to cAMP production such as, for example, a GPCR as described above and measuring the induction of the cAMP mediated cellular response. The cAMP mediated cellular response may be determined by, for example, quantifying the production of cAMP or by monitoring the activation of an endogenous cAMP responsive gene and/or of a cotransfected cAMP responsive reporter gene. A detailed method for identifying a suitable cell line is described, for instance, in Example 1.

The cAMP-responsive element present in the regulatory elements which drive expression of the reporter gene on the first vector may in principle be any element known to respond to elevated levels of intracellular cAMP with an increase of transcription rate of a cis-linked sequence. Such cAMP-responsive elements are known, for example, from the genes encoding peptide hormones, for example somatostatin and corticotropin releasing hormone and are described in Spengler et al., Mol. Endocrinology 6 (1992), 1931–1941; Comb et al., Nature 323 (1986), 353–356; Roesler et al., J. Biol. Chem. 263 (1988), 9063–9066; Karin, Trends Genet. 5 (1989), 65–67 and Lalli and Sassone-Corsi, J. Biol. Chem. 269 (1994), 17359–17362. Preferably, the cAMP-responsive element has the nucleotide sequence of the consensus sequence of cAMP-responsive elements described in the literature. Most preferably, the cAMP-responsive element is one known from a human corticotropin releasing hormone gene which is, advantageously, flanked by sequences naturally surrounding it. Advantageous is also the use of a cAMP-responsive element comprising the consensus sequence of an AP1 element or a degenerated version thereof.

The regulatory elements comprising the cAMP-responsive element(s) and which direct expression of the reporter gene in the transfected cells, may be any suitable elements capable of directing expression in the chosen cells. These elements normally comprise a promoter sequence, in particular a minimal promoter, preferably one which comprises (a) a TATA or a CAAT box, preferably in conjunction with an Sp1-dependent activator, or (b) an initiator element (Inr) in conjunction with an Sp1-dependent activator. In a preferred embodiment the regulatory elements are derived from mammary mouse tumor virus (MMTV) promoter.

The reporter gene present in the first vector may be any suitable reporter gene the expression of which can be detected in the transfected cells. Preferably, a reporter gene is chosen the expression of which can be easily detected, for example, by photometric or fluorometric methods, isotopic labelling or by a staining reaction. Examples for reporter genes preferably used in the method according to the invention are those coding for chloramphenicol-acetyltransferase (CAT), β-galactosidase (β-Gal), secreted alkaline phosphatase (SEAP) or growth hormone (GH). Most preferably, a gene coding for luciferase is used.

The term "pool of expression vectors" in step (i) (b) of the method according to the invention is meant to be understood as a plurality of vector molecules which are either identical or not and which are adapted for expression in the transfected cells. Such vector molecules comprise regulatory elements which are capable of directing expression of a linked sequence in the transfected cells. Furthermore, these vector molecules comprise nucleic acid sequences linked to said regulatory elements which code for a gene product and which may either be identical or different in the members of the vector pool. The vectors of said vector pool may furthermore comprise sequences which ensure replication in prokaryotic host cells as well as sequences which ensure replication in the transfected eukaryotic cells. Such a pool of expression vectors may be, for example, a cDNA library or a genomic library cloned in expression vectors suitable for expression in the transfected cells.

In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1(GIBCO BRL).

In a preferred embodiment the nucleic acid molecules present in the vectors of the vector pool are cDNA molecules. In particular, said cDNA may be prepared from RNA obtained from any organism or tissue, namely from any animal, bacterial, fungal or plant cells or from viruses. Most preferably, the RNA is obtained form mammalian cells. In such case the RNA is preferably derived from a specific tissue or organ of a mammal, e.g., intestine, stomach, lung, adrenal gland, kidney, mammary gland, prostate, testis, most preferably said tissue is pituitary gland, brain or ovary.

If a vector pool is identified in step (iii) of the method according to the invention then it is either possible to isolate from the original pool of the so-identified vector pool the nucleic acid molecules present in the vectors of the vector pool and characterize the encoded products or one can further subdivide the original vector pool, for example, if it consists of vectors with a plurality of different inserts, so as to reduce the number of different vectors per pool and repeat the method with the subdivisions of the original pool. Depending on the complexity of the pool this can be done for several times, preferably so often until the vector pool identified in step (iii) of the method only comprises a limited number of vectors which differ with respect to their inserted nucleic acid molecule. Normally the vector pool used in step (i) for transfecting the cells has previously been isolated from a mixture of bacteria harboring different vectors and which, thus, constitute a kind of library. Subdivision of the vector pool for the purpose of step (iii) of the method can therefore be achieved by subdividing said library comprising the bacteria so that the diversity of the vectors with respect to the inserted nucleic acid sequences is lower in the subdivisions than in the original library. From these subdivisions of the library the expression vectors can then be isolated. These isolates then represent subdivisions of the original vector pool.

The nucleic acid molecules present in vectors of a vector pool identified by (iii) of the method according to the invention can be isolated from the vectors, e.g. by digestion with suitable restriction enzymes and can be further characterized, for example by restriction mapping, sequencing etc. The expression products of the thus obtained nucleic acid molecules are then tested for their tumor suppressor activity. This can be done, for example, by measuring the suppression of colony formation of transformed cell lines transfected with a TSG expressing vector. Furthermore, an inducible expression system may be employed to measure the suppression of growth of tumor cells which are stably transfected with an inducible TSG. After induction of TSG expression the growth of the tumor cells can be monitored and compared to non-TSG expressing tumor cells. An example of an inducible expression system is the tetracycline-regulated gene expression but others may be used as well, for example, heavy metal inducible expression systems. The suppressor activity of the putative TSG can also be detected by assaying its ability of suppressing anchorage-independent cell growth after induction of the TSG of the stably transfected tumor cells. Furthermore, the loss of tumorigenicity under expression of the TSG can be tested, for example, by implanting the tumor cells harboring an inducible TSG in nude mice and monitoring tumor development after induction of TSG expression. The capability of TSGs of recruiting apoptotic programs to inhibit growth of tumor cells is evidenced, for example, by the failure of the induced TSG expressing cells to convert MTT, their shrinking in size, their abundance in phase contrast microscopy, blebbing of their membrane, and rounding up of the cells before detaching from the plates. The cell death may also be accompanied by fragmentation of the DNA into a ladder of regular subunits. All the methods referred to are well known in the art and are described in the Examples of the present application and/or are described in Zhou et al., Proc. Natl. Acad. Sci. USA 91 (1994), 4165–4169; Chen et al., Science 250 (1990), 1576–1580; Baker et al., Science 249 (1990), 912–915; Diller et al., Mol. Cell. Biol. 10 (1990), 5772–5781; Casey et al., Oncogene 6 (1991), 1791–1797; Cheng et al., Cancer Research (1992), 222–226; Wang and Prives, Nature 376 (1995), 88–91; Mercer et al., Proc. Natl. Acad. Sci. USA 87 (1990), 6166–6170; Antelman et al., Oncogene 10 (1995), 697–704; Gossen et al., Trends Biotech. 12 (1994), 58–62; Gossen and Bujard, Proc. Natl. Acad. Sci. USA 89 (1992), 5547–5551.

The expression products of the identified nucleic acid molecules can be furthermore characterized by expressing them in prokaryotic host cells and purifying them. Subsequently, enzymatic and/or other biological activities can be determined by in-vitro assays. Expression in eukaryotic host cells or in-vitro transcription and translation systems may furthermore provide information about possible phosphorylation and/or glycosylation patterns etc.

As demonstrated in the examples of the present invention, the above-described method is suitable to identify and isolate nucleic acid molecules which encode proteins having the biological activity of a tumor suppressor.

Thus, in another aspect the present invention relates to nucleic acid molecules obtainable by a method according to the invention which encode a protein or polypeptide having tumor suppressor activity. Examples for such nucleic acid molecules are those described above. In a preferred embodiment the nucleic acid molecules according to the invention are DNA molecules, most preferably cDNA molecules.

Nucleic acid molecules according to the invention can be derived from any organism, namely from animals, plants, fungi, bacteria or viruses. In a preferred embodiment the nucleic acid molecules according to the invention are derived from a mammal, most preferably form a human or a mouse.

With the help of nucleic acid molecules identified and isolated by the method according to the invention it is possible to isolate the same or related molecules from the same or different organisms, for example, by screening genomic or cDNA libraries with the nucleic acid molecules isolated according to described method as a probe.

Thus, the present invention also relates to nucleic acid molecules which hybridize to a nucleic acid according to the invention as described above and which code for a protein having tumor suppressor activity.

Furthermore, the present invention relates to nucleic acid molecules which hybridize to a nucleic acid molecule according to the invention as described above and which encode a mutated version of a polypeptide encoded by a nucleic acid molecule as described above which has lost its tumor suppressor activity.

Furthermore, the present invention relates to nucleic acid molecules which represent or comprise the complementary strand of any of the above described nucleic acid molecules or a part thereof. Such a molecule may either be a desoxyribonucleic acid or a ribonucleic acid. Such molecules comprise, for example, antisense RNA. These molecules may furthermore be linked to sequences which when transcribed code for a ribozyme thereby producing a ribozyme which specifically cuts transcripts of nucleic acid molecules according to the invention.

The present invention also relates to nucleic acids molecules of at least 15 nucleotides in length which specifically hybridize to any one of the aforementioned nucleic acid molecules or to a complementary strand thereof. Said nucleic acid molecules may be used, for example, as probes for the detection of a TSG according to the invention or its mRNA. In a preferred embodiment said nucleic acid molecules are labeled. Methods for the detection of nucleic acids are well known in the art, e.g., Southern and northern blotting, PCR, primer extension. In another preferred embodiment said nucleic acid molecules may be used for the suppression of TSG expression.

Furthermore, the present invention relates to a vector comprising a nucleic acid molecule according to the invention. Examples for such vectors are pUC18, pBR322, pBlue-Script.

In a preferred embodiment the nucleic acid molecule present in the vector is operatively linked to regulatory elements permitting expression in prokaryotic or eukaryotic host cells. Possible regulatory elements permitting expression in prokaryotic host cells comprise, e.g., the lac or trp promoter in (*E. coli*), and examples for regulatory elements permitting expression in eukaryotic host cells are the AOX1 or GAL1 promoter in yeast or the CMV-, SV40-, RSV-promoter (*Rous sarcoma* virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule.

The invention also relates to a host cell comprising a vector according to the invention. In this context, the host cell may be a bacterial, fungal, plant or animal cell. In a preferred embodiment the host cell is a mammalian cell.

In a further embodiment the invention relates to a method for the production of a polypeptide having the biological activity of a tumor suppressor comprising culturing a host cell as defined above under conditions allowing the expression of the polypeptide and recovering the produced polypeptide from the culture. Such methods are described, for example, in LaVallie and McCoy, Curr. Opin. Biotech. 6 (1995), 501–506; Wong, Curr. Opin. Biotech. 6 (1995), 517–522; Romanos, Curr. Opin. Biotech. 6 (1995), 527–533; Keränen and Penttilä, Curr. Opin. Biotech. 6 (1995), 534–537; Williams et al., Curr. Opin. Biotech. 6 (1995), 538–542; Davies, Curr. Opin. Biotech. 6 (1995), 543–547; Holmgren, Annu. Rev. Biochem. 54 (1985) 237–271 or LaVallie et al., Bio/Technology 11 (1993) 187–193.

Furthermore, the invention relates to a polypeptide encoded by a nucleic acid molecule according to the invention or produced by the above-described method, which has tumor suppressor activity.

In this context it is also understood that the polypeptides according to the invention may be further modified by conventional methods known in the art. By providing the polypeptides according to the present invention it is also possible to determine the portions relevant for their biological activity, namely their tumor suppressor activity. This may allow the construction of chimeric proteins comprising an amino acid sequence derived from a tumor suppressor protein of the invention which is crucial for tumor suppression and other functional amino acid sequences e.g. nuclear localization signals, transactivating domains, DNA-binding domains, hormone-binding domains, protein tags (GST, GFP, h-myc peptide, Flag, HA peptide) which may be derived from the same or from heterologous proteins.

The present invention also relates to a polypeptide encoded by a nucleic acid molecule according to the invention or produced by the above-described method, which is a mutated version of an above-described polypeptide which has lost its tumor suppressor activity.

The present invention furthermore relates to antibodies specifically recognizing a polypeptide according to the invention which has a tumor suppressor activity. Namely, the invention relates to antibodies which specifically recognize polypeptides according to the invention irrespective of whether they are functional tumor suppressors or whether they are mutated forms which have lost their tumor suppressor activity.

In a preferred embodiment the antibody specifically recognizes a polypeptide according to the invention which has tumor suppressor activity but does not recognize a polypeptide which is a mutated version of such a polypeptide and which has lost its tumor suppressor activity.

In another preferred embodiment the antibody specifically recognizes the mutated form which has lost its tumor suppressor activity but not the corresponding polypeptide having tumor suppressor activity.

In a preferred embodiment said antibody is a monoclonal antibody.

Anti-tumor suppressor protein antibodies can be prepared by well known methods using a purified tumor suppressor protein according to the invention or a synthetic fragment derived therefrom as an antigen. Monoclonal antibodies can be prepared, for example, by the techniques as described in Köhler and Milstein, Nature 256 (1975), 495, and Galfré, Meth. Enzymol. 73 (1981), 3, which comprise the fusion of mouse myeloma cells to spleen cells derived from immunized mammals.

Moreover, the present invention relates to a pharmaceutical composition comprising at least one of the aforementioned nucleic acid molecules, vectors, polypeptides and/or antibodies according to the invention either alone or in combination, and optionally a pharmaceutically acceptable carrier or excipient.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. The pharmaceutical compositions can be administered to the subject at a suitable dose. Administration of the suitable compositions may be effected by different ways, e.g. by intravenous, intraperetoneal, subcutaneous, intramuscular, topical or intradermal administration.

The pharmaceutical compositions according to the invention can be used for the prevention or treatment of different kinds of diseases, for example, cancer, namely benign or malignant tumors, of acquired or inborn neuronal disorders, neurodegenerations and related disorders. With respect to the prevention or treatment of tumors, said tumors are preferably derived from endocrine or neuronal tissues, i.e. intestine, stomach, lung, adrenal gland, kidney, mammary gland, prostate, testis, most preferably said tissue is colon, pancreas, thyroid, pituitary gland, brain, breast or ovary.

In a first aspect it is possible to use a pharmaceutical composition which comprises a nucleotide sequence which encodes a non-mutated form of a protein having tumor suppressor activity for gene therapy. As described above tumors or other diseases often evolve when cells lose both functional copies of a tumor suppressor gene. In such a case introduction of functional copies of the corresponding gene may help to ameliorate the situation. For example research pertaining to gene transfer into cells of the nervous system is one of the fastest growing fields in neuroscience. Gene therapy, which is based on introducing therapeutic genes into cells of the nervous system by ex-vivo or in-vivo techniques is one of the most important applications of gene transfer. Gene therapy of the nervous system could be applied for three general purposes: genetic diseases, acquired degenerative encephalopathies, and control of malignant neoplasia.

In genetic diseases the introduction of a normal or a functionally adequate allele of a mutated nuclear gene represents gene-replacement therapy, which is applicable mainly to monogenetic recessive disorders.

In the field of neurobiology, for example, it has long been recognized that the balance between cellular proliferation and cell death during embryogenesis is a key factor in formation of the central nervous system (CNS). The recent definition of molecular mechanisms that drive the cell-division cycle and programmed cell dead provides an opportunity to investigate the molecular interactions that co-ordinate cell-cycle regulation with CNS-pattern formation, neural differentiation and histiogenesis. It appears evident that not only is the cell-division cycle regulated by developmentally controlled molecular signals to halt or proceed, but gene products that drive the cycle can also influence the course of neural differentiation and apoptosis. The neurotrophic strategy for the regulation of neuronal numbers may be only one example of a general mechanism that help to regulate the numbers of many other vertebrate cell types, which also require signals from other cells to survive. These survival signals seem to act by suppressing an intrinsic cell suicide program, the protein components of which are apparently expressed constitutively in most cell types. TSGs have emerged during the last years as major players in this area. Mice deficient for Rb revealed massive neuronal cell death due to the failure to stop cell division. A subset of p53-deficient mice (8 to 16%) exhibit exencephaly and a large population (40%) of Brca1-deficient mice embryos suffered to varying degrees of spina bifida and anencephalopathy. In addition, these animals displayed a disorganisation of the neuroepithelium with signs of rapid proliferation and excessive cell death. Thus, it appears as if TSGs are intimately involved in CNS formation and that the balance between growth-constraining elements and neurotrophic support is a key event in formation of neuronal architecture. In this respect, nucleic acid molecules according to the invention which code for proteins with tumor suppressor activity are potential candidates to participate in these processes. Importantly, the nucleotide sequence of SEQ ID NO. 1 which encodes a novel tumor suppressor hybridizes to total RNA isolated from different brain areas of the mature brain. This opens the perspective that the subtle balance between promoters of apoptosis like the protein encoded by SEQ ID NO. 1 and protectors like neurotrophins safeguard functional integrity of the mature brain. An increasing list of neurodegenerative disorders including Alzheimer disease and Chorea Huntington have been reported to reveal increased incidence of apoptotic cell death. In this view gene targeting of nucleic acid molecules coding for a protein having the amino acid sequence as depicted in SEQ ID NO. 2 or nucleic acid molecules coding for related proteins of the invention bears the potential promise to mitigate apoptotic cell death under various circumstances and to increase sensitivity to neurotrophic treatments aimed to preserve neuronal cell number and neuronal viability.

Furthermore, recent reports indicated that p53-dependent apoptosis modulates the cytotoxic effects of common antitumor agents such as ionizing radiation, fluorouracil, etoposide, and doxrubicin. Cells lacking wild-type p53 are resistant to these agents, whereas cells expressing wild-type p53 are sensitive to them and undergo cell death by apoptosis. These observations raise the exciting prospect that p53 mutations may provide a genetic basis for drug resistance. In the presence of p53, oncogene-expressing cells can form tumors, but cell survival is limited by their increased susceptibility to apoptosis. Conversely, p53 loss contributes directly to immortalization and tumorgenesis, probably by abrogating an intrinsic senescence program. As a consequence, selection against p53 often occurs late in tumor progression. Anticancer agents may simply activate the apoptotic program intrinsic to these sensitized cells. These observations predict that reintroduction of normal tumor suppressor function into tumors harboring mutations in tumor suppressor genes will enhance apoptosis after radiation or chemotherapy, an approach that has proved successful for cisplatin in a lung carcinoma cell line.

Since it was observed that introduction of a nucleic acid molecule according to the invention caused apoptotic cell death in transformed cell lines, which in part exceeded the one caused by p53, these novel TSGs present a powerful option of high potential interest in gene therapy experiments. Though p53 and the protein encoded by SEQ ID NO. 1 induce at a descriptive level the same responses, namely cell-cycle regulation and cell death, the underlying molecular routes diverge. This observation originates from the fact that the DNA-binding domain of the protein encoded by SEQ ID NO. 1 is organized in a typical zinc finger structure, which is unrelated to the central DNA-binding domain of p53. Therefore, the protein encoded by SEQ ID NO. 1 and related proteins could replace p53 in gene therapy strategies. Importantly p53 seems only to trigger growth arrest and not cell death in some cell types and under some conditions. In line with this view we demonstrated that restoration of inducible p53 function in the p53-negative cell line Saos-2 (human, osteosarcoma) installed preferentially a growth and a comparatively weak apoptotic response, whereas Saos-2 cells became highly apoptosis proficient under expression of the protein encoded by SEQ ID NO. 1. This differential apoptotic response emphasizes the idea that this protein and other TSGs of the invention and p53 supply different molecular routes to apoptosis and open the exciting perspective that apoptosis competency is a tissue-specific encoded genetic program. Conclusively tissue-specific TSGs as those provided by the present invention could encode specific properties to guide tumorigenic cells to apoptotic cell death and their potency to do so could surpass p53 as illustrated for the protein encoded by SEQ ID NO. 1 in Saos-2 cells.

Importantly again, the understanding of p53 function as an example for a tumor suppressor gene suggest a basis for the association between p53 mutations and poor patient prognosis. Thus, p53 mutations, which are with 50% among the most common alterations observed in human cancer, may be a significant impediment to successful cancer therapy. For example, p53 mutations dramatically reduce the probability that patients with B cell chronic lymphocyte leukemia will enter remission after chemotherapy. Similarly evaluation of the status of proteins encoded by nucleic acid molecules according to the invention and related proteins in tumor samples could serve as an decisive parameter for the extent and necessity of surgical resection and the need for adjuvant therapy. In a more general view, the status of nucleic acid molecules according to the invention encoding proteins with the capability to induce apoptosis could become a decisive criteria to develop treatment priorities for individual tumor specisms. In another important aspect the above-mentioned pharmaceutical compositions may be used in immuntherapy. The well-characterized mutations of a TSG also suggest the possibility of immuntherapy or even a cancer vaccine, which would alert the body's immune system to the mutant forms of the protein. Cross-reactivity to wild-type forms has to be considered as a potential unwanted side-effect with profound implications since abating wild-type function through uncontrolled autoimmunoreactivity would dramatically enhance the risk of additional tumor formation. In this regard, it is advantageous to use tissue specific TSGs, such as the one represented in SEQ ID NO. 1, since in this way the risk of the above-mentioned unwanted side-effect can be substantially lowered.

Suitable vectors and methods for the in-vitro or in-vivo gene therapy are described in the literature and are well-known to the person skilled in the art.

In another aspect it is possible that the pharmaceutical compositions comprise the functional proteins encoded by the nucleic acid molecules according to the invention or proteins which represent mutated versions of these proteins which occur in various diseases. These compositions may either be useful to restore normal tumor suppressor activity in cells which have lost both functional copies of the relevant gene or for immuntherapy as already described above.

Furthermore, the use of pharmaceutical compositions which comprise antisense-oligonucleotides which specifically hybridize to RNA encoding mutated versions of a tumor suppressor according to the invention or which comprise antibodies specifically recognizing such mutated versions but not the functional wild-type form is conceivable in cases in which the concentration of the mutated form in the cells should be reduced. The pharmaceutical compositions according to the invention can be used for the treatment of various kinds of diseases. Thus, the present invention also relates to methods for the treatment or prevention of tumors or neuronal disorders or for the delay of the reoccurrence of tumors or neuronal disorders which comprises the administration of an effective dose of a pharmaceutical composition according to the invention to the subject.

Furthermore, any of the aforementioned nucleic acid molecules, vectors, polypeptides and/or antibodies according to the invention either alone or in combination can be used for the preparation of a pharmaceutical composition for treating, preventing and/or delaying of reoccurrence of a disease in a subject. Preferably, said disease is a tumor or a neuronal disorder, for example, a tumor or a neuronal disorder as described above.

The invention also relates to a diagnostic composition comprising at least one of the aforementioned nucleic acid molecules, vectors, polypeptides, and/or antibodies according to the invention, and optionally suitable means for detection.

Said diagnostic compositions may be used for methods for detecting expression of a tumor suppressor by detecting the presence of mRNA coding for a tumor suppressor which comprises obtaining mRNA from a cell and contacting the mRNA so obtained with a probe comprising a nucleic acid molecule of at least 15 nucleotides capable of specifically hybridizing with a nucleic acid molecule encoding a tumor suppressor under hybridizing conditions, detecting the presence of mRNA hybridized to the probe, and thereby detecting the expression of the tumor suppressor by the cell.

Furthermore, the invention comprises methods of detecting the presence of a tumor suppressor of the present invention in a sample, for example, a cell sample, which comprises obtaining a cell sample from the subject, contacting said sample with one of the aforementioned antibodies under conditions permitting binding of the antibody to the tumor suppressor, detecting the presence of the antibody so bound, for example, using immuno assay techniques, for example, radioimmunoassay or enzymeimmunoassay. Furthermore, one may specifically detect and distinguish polypeptides which are functional tumor suppressors from mutated forms which have lost or altered their tumor suppressor activity by using an antibody which either specifically recognizes a polypeptide which has tumor suppressor activity but does not recognize an inactive form thereof or which specifically recognizes an inactive form but not the corresponding polypeptide having tumor suppressor activity. The antibodies of the present invention may also be used in affinity chromatography for purifying the polypeptides of the present invention and isolating them from various sources.

The invention also relates to a method for diagnosing in a subject a predisposition to a tumor or a disorder associated with the expression of a tumor suppressor allele which comprises isolating DNA from victims of the tumor or the disorder associated with the expression of a tumor suppressor; digesting the isolated DNA with at least one restriction enzyme; electrophoretically separating the resulting DNA fragments on a sizing gel; contacting the resulting gel with a nucleic acid probe as described above capable of specifically hybridizing to DNA encoding a tumor suppressor and labeled with a detectable marker; detecting labeled bands on the gel which have hybridized to the labeled probe to create a band pattern specific to the DNA of victims of the tumor or the disorder associated with the expression of a tumor suppressor; preparing the subject's DNA according to the above-mentioned steps to produce detectable labeled bands on a gel; and comparing the band pattern specific to the DNA of victims of the tumor or the disorder associated with the expression of a tumor suppressor and the subject's DNA to determine whether the patterns are the same or different and to diagnose thereby predisposition to the tumor or the disorder if the patterns are the same. The detectable markers of the present invention may be labeled with commonly employed radioactive labels, such as, for example, $^{32}$P and $^{35}$S, although other labels such as biotin or mercury may be employed as well. Various methods well-known to the person skilled in the art may be used to label the detectable markers. For example, DNA sequences and RNA sequences may be labeled with $^{32}$P or $^{35}$S using the random primer method. Once a suitable detectable marker has been obtained, various methods well-known to the person skilled in the art may be employed for contacting the detectable marker with the sample of interest. For example, DNA-DNA, RNA-RNA and DNA-RNA hybridizations may be performed using standard procedures. Various methods for the detection of nucleic acids are well-known in the art, e.g., Southern and northern blotting, PCR, primer extension and the like. Furthermore, the mRNA, cRNA, cDNA or genomic DNA obtained from the subject may be sequenced to identify mutations which may be characteristic fingerprints of TSG mutations in tumors or disorders associated with the expression of TSG or mutated versions thereof. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above.

It is furthermore possible to use the TSGs and proteins according to the invention for the design of "killer genes" (Da Costa et al., Proc. Natl. Acad. Sci. USA 93 (1996), 4192–4196). It has become clear that tumorigenesis is driven by alterations in genes that control cell growth and cell death. Gene therapy could be aimed at specifically kill tumor cells expressing mutated forms of tumor suppressor genes. In outline, the target protein, i.e. the mutated tumor suppressor, binds to exogenously introduced gene products, resulting in transcriptional activation of a toxic gene. This strategy may be generally applicable to neoplastic disease in which the underlying patterns of genetic alterations or abnormal gene expression are known (Da Costa et al., Proc. Natl. Acad. Sci. USA 93 (1996), 4192–4196).

Conceivable is also the restoration of the wild-type conformation of mutated tumor suppressor proteins.

Some genetic changes lead to altered protein conformational states. For example, mutant p53 proteins possess a tertiary structure that renders them far less capable of binding to their wild-type DNA recognition elements. Restoring the normal or regulated conformation of mutated proteins is the most elegant and specific means to correct these molecular defects, although it is difficult. Of particular interest in this regard is the zinc finger structure of the protein encoded by SEQ ID NO. 1 if the DNA-binding potency is reduced in mutated proteins. The fact that the nucleic acid molecule having the nucleotide sequence as depicted in SEQ ID NO. 1 are expressed in a tissue-specific manner deserves particular attention. All pharmacological manipulations aimed at restoration of wild-type conformation p53, bear the risk to interfere with the wild-type function of this tumor suppressor in neighboring non-tumorgenic tissues with profound side-effects. In contrast the targeting of tissue-specific TSGs could remarkably extend the applicability of a targeting approach, since considerable higher concentrations of the molecules and/or long-lasting derivatives can be employed at a lowered risks for demetrial side-effects.

Thus, the nucleic acid molecules and encoded proteins of the present invention may also be used to design and/or identify molecules which are capable of activating the wild-type function of a tumor suppressor. These molecules may be small organic compounds, antibodies, petidomimics, PNAs or peptides (Milner, Nature Medicine 1 (1995), 879–880; Hupp et al., Cell 83 (1995), 237–245; Gibbs and Oliff, Cell 79 (1994), 193–198).

(C) Expression of Bop1 mRNA in mouse tissue. Bop1 distribution was assessed by northern blot analysis of total RNA prepared from different brain regions (olfactory bulb (Olf), frontal cortex (fCx), occipital cortex (oCx), hippocampus (Hip), hypothalamus-thalamus (HyT), brain stem (BSt), cerebellum (Crb) and peripheral tissues (anterior pituitary gland (Pit)), heart (Hea), liver (Liv), stomach (Sto), intestine (Int), kidney (Kid), adrenal gland (Adr), spleen (Spl), lung (Lun)). Ethidium bromide staining of the gel is shown in the insert to document equal and intact amounts of each RNA preparation.

FIG. 2A–2D: Bop1 and p53 Alter Proliferation of LLC-PK1 and Saos-2 Cells

Anhydrotetracycline(ATc)-regulated expression of Bop1 and p53 was established in LLC-PK1 and Saos-2 cells.

(A) Cell counts of the parent tTA clones (L-tTA and S-tTA) in comparison to Bop1- and p53-expressing LLC-PK1 (L-Bop and L-p53, respectively) and Saos-2 (S-Bop and S-p53, respectively) clones in the presence (+) and absence (–) of ATc.

(B) Bop1 and p53 inhibit DNA-synthesis (BrdU) and cell viability (MTT). For each time point, BrdU incorporation or formazan blue formation were measured in the absence (–) or the presence (+) of ATc.

(C) Growth inhibition by Bop1 and p53 is serum independent. Cells were grown in the presence of the indicated amount of fetal bovine serum (10% or 0.1%) and in the presence (+) or absence (–) of ATc.

(D) Growth inhibition by Bop1 and p53 is reversible. Cells were seeded in Atc-containing medium, grown in the absence of ATc for 2 days before medium was renewed (arrowhead) with medium containing (±) or lacking (–/–) ATc.

FIGS. 3A–3D: Bop1 and p53 Inhibit Soft Agar Colony Formation

Bop1 (L-Bop and S-Bop) and p53 (L-p53 and S-p53) clones were grown in the presence of ATc before plating into soft agar at densities of $1 \times 10^5$ (No. 1+4), $5 \times 10^4$ (No. 2+5) and $2.5 \times 10^4$ (No. 3+6) cells per well in six-well plates. The repressor ATc was included in the upper row (+) and was omitted in the lower row (–). For photography on day 10, the soft agar was overlaid with MTT for 4 hr. Pictures shown are representative of three to five independent experiments.

Figures 1, 4A:
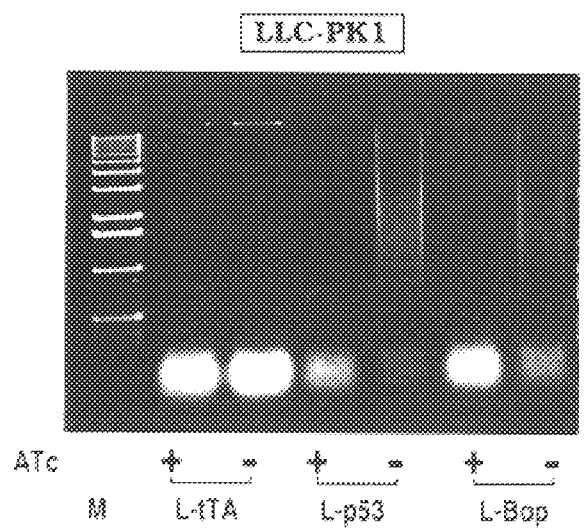
Figures 2, 4A:
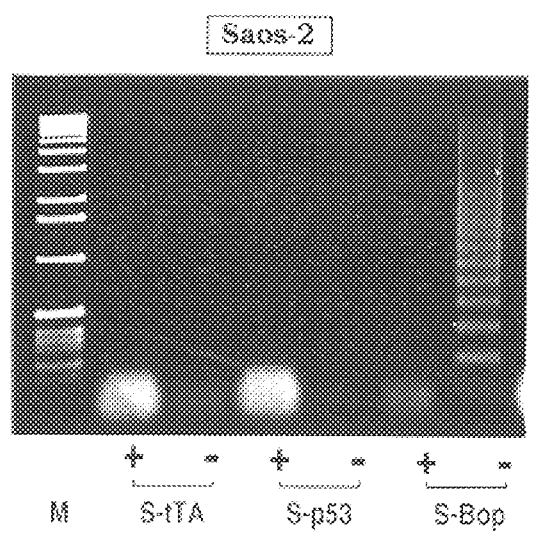

FIG. 4A–4C: Bop1 and p53 Induce Apoptotic Cell Death (A) DNA laddering. Genomic DNA was isolated from Bop1 (L-Bop and S-Bop) and p53 (L-p53 and S-p53) expressing clones grown in the presence (+) or absence (–) of ATc for 3 days, centrifugated and soluble DNA was subjected to agarose gel electrophoresis and stained with ethidium bromide.

(B) Fluorescence microscopy of Bop1 and p53 clones stained with ethidium bromide and acridine orange. Cells (a: L-Bop; b: L-p53; c: S-Bop; d: S-p53) were grown in the absence of ATc for 3 days. Floating cells were collected, incubated with ethidium bromide and examined by fluorescence microscopy (510–550 nm; ×1000).

(C) DNA end labeling. S-Bop (Bop1) and S-p53 (p53) cells were grown for 3 days in the presence (black) or absence (grey) of ATc. Permeabilized cells were subjected to terminal transferase end labeling (TUNEL) in the presence of digoxigenin-labeled dUTP. Cells were then incubated with fluorescein-conjugated antidigoxigenin antiserum and subjected to flow cytometry.

FIG. 5A–5C: Bop1 and p53 Regulate Cell Cycle Distribution (A) Induction of G1 arrest by Bop1 and G2/M arrest by p53. S-Bop (upper panels) and S-p53 (lower panels) were grown in the presence (left) or absence (right) of ATc for 3 days. Propidium iodide-stained cells were analyzed by flow cytometry to determine DNA content. Bop1 reduced the proportion of S-populations in S phase and G2/M phase from 37.8% and 17.5% to 24.5% and 12.6%, respectively and increased cell population in G1 from 44.7% for the repressed state to 63.0% for the expressed state of S-Bop. For p53 a decrease in G1 and S phase from 39.4% to 31.8% and from 43.7% to 35.0% was observed, which was followed by a clear increase in G2/M from 16.9% to 33.2%.

(B) G1-Arrest by Bop1 is independent of $p21^{Waf1}$ expression. S-tTA (tTA), S-p53 (p53) and S-Bop(Bop1) cells were grown in the presence (+) or absence (–) of ATc for 3 days. Western blots of total cell lysates were performed with anti-p21, anti-p53 and anti-GST-Bop1ΔZF antisera.

(C) Apoptotic cell death following Bop1 and p53 expression is unrelated to the cell cycle. TUNEL was carried out on permeabilized S-Bop (Bop1, upper panels) and S-p53 (p53, lower panels) cells grown in the presence (left) or absence (right) of ATc for 3 days. Subsequent staining with propidium iodide allowed simultaneous assessment of DNA content and apoptosis by flow cytometry. Grey dots in the boxed area represent cells with high TUNEL fluorescence and hence apoptotic. Dots in different shades of grey outside the boxed area correspond to living cells in G1 (bottom), S and G2/M (top) phase of the cell cycle. Apoptotic fluorescence threshold was set so that less than 5% of S-tTA cells grown in the presence or absence of ATc were apoptotic (data not shown). Apoptotic cells in the presence of ATc represent less than 5% of the cells in the case of S-Bop and less than 1% for S-p53. In the absence of ATc, 70% of S-Bop (65% of S-p53 resp.) cells displayed enhanced or high TUNEL fluorescence.

FIG. 6A–6D: Transfer of PVR1 Gene Regulation through Bop1 Zinc Finger Domain and Nuclear Localization of Bop1

(A) Schematic representation of Bop1/steroid receptor hybrids. Abbreviations used are G and M for human glucocorticoid (GR) and mineralocorticoid receptor (MR) domains, respectively. The transactivation domain of the GR is represented by a hatched box, the MR hormone binding domain by a black box, and the MR DNA-binding domain by grey box with the two zinc fingers indicated by vertical lines. The numbers above each box indicate amino acids.

(B) The zinc finger domain of Bop1 confers regulation of the PVR1 gene. Native Bop1 and p53 (left) or the hybrid $GB_ZM$ (right) cDNAs were co-transfected with the cAMP-responsive reporter pΔMC16LUC into LLC-PK1 cells ($2 \times 10^6$) and plated with aldosterone (Aldo; $10^{-9}M$) or spironolactone (Spiro; $10^{-7}M$).

PACAP-38 ($10^{-9}$M) was added the next day for 4 hr before harvesting the cells. To calculate induction ratios, luciferase activity was standardized on MTT values.

(C) Regulation of PVR1 by Bop1 requires transactivation (left). The construct $\Delta B_Z M$ is truncated for the GR transactivation domain and was tested under the same conditions as described above. Cytoplasmatic trapping of Bop1 prevents transactivation of the PVR1 gene (right). The native Bop1 cDNA was fused to the hormone-binding domain of the MR to create $Bop_X M$. Transfected LLC-PK1 cells ($2 \times 10^6$) were replated in charcoal-treated serum and aldosterone or spironolactone were added separately. PACAP-38 ($10^{-9}$M) was added next day for 4 hr before cells were harvested. To calculate induction ratios luciferase activity was standardized with MTT values.

(D) Bop1 is a nuclear protein. S-Bop cells were grown in the presence or absence of ATc for three days and simultaneously immunostained with rhodamine-conjugated phalloidin to stain actin filaments and with a rabbit antiserum raised against a GST-Bop1$\Delta$ZF fusion protein. The grey bar represents 25 μm.

DESCRIPTION OF THE INVENTION

EXAMPLE 1

Cloning, Structural Analysis and Tissue Distribution of the TSG Bop 1

In order to isolate DNAs coding for different receptors positively coupled to adenylyl cyclase, we used a recently described expression cloning method (Spengler et al., Nature 365 (1993), 170–175). This method is based on transcriptional induction of a cAMP-responsive luciferase reporter gene by stimulation of adenylyl cyclase through activated target receptors.

Pools of clones from a mouse corticotroph pituitary tumor cell line (AtT-20) (Spengler et al., Nature 365 (1993), 170–175) cDNA library and from a new-born rat colliculi library were co-transfected with a cAMP-responsive reporter into LLC-PK1 cells according to the functional expression transductory cloning technique (FETCH).

This expression cloning technique relies on the co-transfection of pools of clones from a cDNA-expression library with a cAMP-responsive reporter into a mammalian cell line, most preferably LLC-PK1 cells.

In a previous series of studies we noted that a cAMP-responsive element derived from the hCRH-gene promoter conferred regulation by cAMP to heterologous promoters (Spengler et al., Mol. Endocrinology 6 (1992), 1931–1941). Further experiments demonstrated, that basal and induced expression depended strictly on the promoter context and the cell line employed. In this view a modified mammary mouse tumor virus promoter ($\Delta$MTV) proved to be exceptional in combining a low level of basal expression with strong induction ratios in various cell lines tested including CV-1 (monkey kidney fibroblast), JAR (human choriocharcinoma), SK-N-MC (human neuroblastoma) and AtT-20 (mouse anterior pituitary) (Spengler et al., Mol. Endocrinology 6 (1992), 1931–1941). Properties of this reporter were further improved by increase of the number of CREs. These modifications allowed a synergistic enhancement in the response to cAMP approaching an induction plateau at a critical number of eight 5' to 3' end inserted copies without change in the basal levels of expression of this construct. Any further extension of the numbers of CREs resulted in an adversive effect due to squelching of TATA-box mediated basal levels of expression. To circumvent this limitation, we constructed by PCR a construct designated p$\Delta$MC16LUC, which contained a duplication of the cAMP-responsive region 5'-CRE$_8$-TATA-3'.

A panel of cell lines was screened to identify those combining efficient expression from the pRK vector (CMV promoter and CMV enhancer) with high transfection efficiency and with highest responsiveness of the reporter to cAMP. In a preliminary survey, we confirmed in Northern blot experiments that expression from the pRK vector in LLC-PK1 cells was clearly superior to other cell lines used in standard expression cloning techniques e.g. Cos-1 and 293 cells. According to general view highest levels of expression are considered to provide the best chance to detect a specific signal against background noise. Therefore, COS cells are the model of choice in expression cloning strategies allowing replication of transfected cDNAs and resulting in high amounts of proteins of interest, which can be identified by the respective ligand or antibody. Yet, COS cells were poorly responsive to cAMP in regard to induction of the reporter plasmid, so that we investigated in the next step electroporation parameters in LLC-PK1 cells to obtain high transfection efficiency (number of transfected cells). Electrotransfection parameters (voltage, capacitance, resistance, transfection volume, electrodes, buffer composition) were varied systematically and evaluated semi-quantitatively by in situ staining of galactosidase activity of the co-transfected plasmid pCH110, which encodes the β-galactosidase gene under the control of the SV40 promoter. As expected, transient expression levels and transfection efficiency increased linearly to higher field-strengths. In a second series of experiments, we tested the range of induction observed for co-transfection of p$\Delta$MC16LUC with a control plasmid encoding a G-protein coupled receptor expressed from the pRK vector. Importantly, the highest induction ratios obtained deviated clearly from the parameters suggested by in situ staining. Strikingly, under conditions revealing expression of the marker protein galactosidase in >80% of the cells the response to cAMP was severely impaired in its amplitude. In contrast, those cells revealing moderate levels of unstimulated luciferase activity with typically 40% of the cells being transfected displayed the strongest induction ratios. This finding was further substantiated by the fact that maximal stimulation of the reporter by endogenous vasopressin receptors of the host cell coincides with those settings derived from transfection of a recombinant cDNA encoding a G-protein coupled receptor. Conclusively, highest sensitivity of this system to cAMP is achieved in case recovery following electroporation is maximized, which will by far outpass any advantage of higher levels of transfection efficiency and higher levels of DNA in individual cells. This correlation is acknowledged in the designation functional expression transductory cloning technique (FETCH) to emphasize that identification of target clones depends on expression of functional (full-length) cDNAs, the presence of which is detected by subsequent activation of an endogenous signal transduction pathway and can be monitored by activation of a downstream amplificator, i.e. the reporter gene.

Additional improvements were introduced to reduce further the extent of cell death during electrotransfection and to permit fastest recovery within the time frame pre-set by the decay of the transfected DNA within 48 hr. At this step, cell density proceeding splitting of the cells and in turn numbers seeded proved to determine decisively cell viability and viability-independent set-points of cAMP-responsiveness. For instance, transfection of a confluent plate of LLC-PK1 cells resulted in slightly increased cell death but an almost complete loss of cAMP-responsiveness of the reporter due to a dramatic upregulation of basal levels of expression equivalent to the activity obtained under the induced state. This result indicates that cell-cell contact and in-turn mitotic activity of LLC-PK1 cells controls responsiveness of cAMP-dependent transcription factors activated by G-protein coupled receptors. Therefore we developed an empirical scheme to passage LLC-PK1 cells: On day one, cells were seeded at a density of $3.3 \times 10^4$ cells/cm$^2$ and allowed to grow for 48 hr. Since the doubling time is about 18 hr under exponential growth conditions plates are around 75% confluent on day three, on which medium is renewed. This medium change provides a strong growth stimulus and results 24 hr later in a mild growth arrest due to increasing cell density. Cells for electrotransfection were splitted in the evening at $6.6 \times 10^4$ cells/cm$^2$ and the release from this growth block allowed an enforced mitotic activity 12 hr later with no visible cell death following electroporation, low levels of basal expression of the reporter and an excellent response to stimulation by cAMP. The cells of the stock population were kept under identical conditions (day 1 seeding $3.3 \times 10^4$/cells cm$^2$ cells, day 3 medium renewal, day 4 passaging), which resulted in an accelerated growth behavior. The transition into an optimized transfection competent state required at least two rounds of passages of LLC-PK1 cells under the detailed protocol.

In addition we tested an array of tools described to enhance DNA-uptake and stability (synchronization of cells, butyrate, PEG) or to enhance the responsiveness of the PKA-pathway ($Ca^{++}$-ionophores, PKC-agonists, phosphatase inhibitors) with all of them influencing adversely sensitivity due to reduced cell viability. A notable exception of this rule was the omittance of serum 8 hr after electrotransfection. Although serum was required immediately after electrotransfection during the recovery phase, one wash and replenishment with serum-free medium in the evening resulted in a 2–3-fold increase in cAMP-responsiveness of the system, which was attributable to a lowered basal activity of the reporter.

Following transfection of cDNA pools in LLC-PK1 cells stimulation of endogenous vasopressin receptors and activation of the reporter served as an internal control to evaluate responsiveness of the PKA-pathway and in turn cell viability. Though electroporation reveals a higher reproducibility compared to chemical methods slight variations can considerably distort the interpretation of induction ratios because of the above-mentioned dependence on cAMP-responsiveness. In addition we included as a positive internal control a plasmid encoding the $\beta_1$-adrenergic receptor, which is positively coupled to cAMP-production and was expressed from the same expression cloning vector. Identical aliquots of this control plasmid were added to each pool of cDNAs to be tested and a control pool, which was composed of one clearly negative pool of 2,000 independent clones. The combined information of induction ratios for vasopressin and the $\beta_1$-agonist isoproterenol allowed to discriminate between the following situations:

a) low ratios for vasopressin and isoproterenol point to low cAMP-responsiveness and impaired cell viability.

b) high ratios for vasopressin and low ratios for isoproterenol point to inefficient transfection or degradation of pool DNA c) high ratios for vasopressin and isoproterenol point to optimal transfection.

d) isoproterenol ratio of test pool below the one of the control pool indicate a number of clones >2,000 or a poor quality of the DNA.

e) isoproterenol ratio of test pool above the one of the control pool indicate a number of pools <2,000 leading to an overestimate in the number of independent clones screened.

In the presented scheme the cut-off for each induction ratio obtained for a substance tested has for each pool to be related to the respective ratios obtained for the external vasopressin and the internal isoproterenol control. In this view a PACAP-dependent induction ratio of 3-fold under condition a) has to be considered significant, whereas under condition c) reflects a borderline value. This standardization allows to compare different samples from the same or different experimental settings and is a prerequisite to compare results from retesting of borderline pools or from successive subdivisions of a putatively positive pool.

Separate aliquots of cells were incubated with peptide hormones, including PACAP, 12 hr after electroporation. One pool of clones from the rat colliculi library consistently stimulated luciferase activity in the presence of PACAP and a functional clone encoding the PVR1 receptor was isolated by successive subdivisions (Spengler et al., Nature 365 (1993), 170–175). Subdivision of the pool of clones was achieved by subdividing the cDNA library until the pool of clones represented a substantially homogeneous pool of clones which consistently stimulated luciferase activity. Several other pools displayed the same phenotype, namely a PACAP-dependent stimulation of the reporter gene (data not shown) and the corresponding active clones were isolated by the same subdivision process. Sequencing was carried out by subcloning restriction fragments in pBSBluescript using T3, T7 and internal primers. Two clones from the AtT-20 library (p2195 and p1270) inducing PVR1 expression turned out to encode the same protein (in the scope of the present invention referred to as Bop1).

The isolated cDNA clones p2195 and p1270 contained a 2.8 kb and 4.7 kb insert, respectively. Entire sequencing of clone p2195 revealed a 2790 bp cDNA (shown in SEQ ID NO. 1) encoding an open reading frame of 667 amino acids (shown in SEQ ID NO. 2) giving rise to a protein with a predicted molecular weight of 75 kDa (FIG. 1A). The ATG of AGGCC<u>AT</u>GG (SEQ ID NO. 4) was assigned as initiation codon on the basis of its close match to the CC(A/G) CCATGG (SEQ ID NO. 5) Kozak consensus sequence for favored initiation of translation and the presence of an in-frame TGA stop codon 12 nucleotides upstream (data not shown). Data base searches revealed the presence of seven zinc fingers (Klug and Schwabe, FASEB J. (1995), 597–604) in the N-terminal region of Bop1. However, homologies to other members of the zinc finger protein family were low (30% for the best), with the closest group being the GLI-Krüppel family of zinc finger proteins which have been implicated in normal development and tumor formation (Ruppert et al., Mol. Cell. Biol. 8 (1988), 3104–3113). In particular, the first H/C link (HSRERPFKC (SEQ ID NO. 6)) is in good agreement with the consensus motif for the GLI-Krüppel family (H(S/T)GEKP(F/Y)XC (SEQ ID NO. 7)) (Schuh et al., Cell 47 (1986), 1025–1032). On the other hand, the remaining 459 C-terminal amino acids displayed no significant homologies to sequences in the Swissprot and NBRF-PIR data bases. The central region of the protein (275–383) is characterized by 34 PLE, PMQ or PML repeats, suggestive of a structure known as poly proline type II helix which is considered to be critically involved in protein-protein interactions (Williamson, Biochem. J. 297 (1994), 249–260). The COOH-terminal region is particularly P-, Q- and E-rich, a feature often displayed by transactivation domains of transcription factors. In addition, the presence of a putative phosphorylation site (HSPQK (SEQ ID NO. 8)) for cyclin-dependent kinases (Cdks) located between the second and third zinc finger motif (residues 56–60) as well as a putative PKA-phosphorylation site (KKWT (SEQ ID NO. 9)) at the very C-terminus (residues 663–666) suggests possible regulation by protein kinases.

Figure 1C:
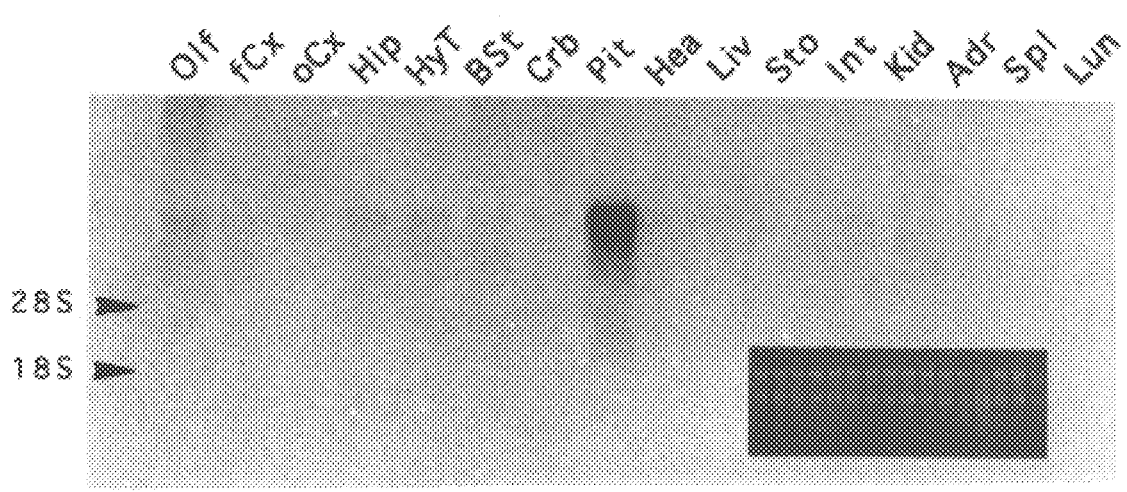
FIGS. 1A–1C: Bop1 Sequence and Tissue Distribution
(A) Sequence of Bop1 protein. Cysteine and histidine residues of the seven zinc finger motifs of the $C_2H_2$ type are boxed. A putative phosphorylation site for cyclin-dependent kinases (Cdks) corresponding to the consensus motif (b/p)(S/T)Pxb located at residues 56–60 is underlined. A putative phosphorylation site for protein kinase A (PKA) at residue 666 is indicated (*).
(B) Schematic representation of Bop1 clones. Clone p2195 and p1270 were derived from the AtT-20 corticotroph tumor cell line. Clone B-16 was isolated from a BALB/c pituitary library and encodes the same protein identified in p2195 and p1270. The coding region of p1270 and B-16 is interrupted at residue 658 by a 630 bp insertion. The sequences at the boundaries of this insertion are displayed in the lower part of the figure and are in excellent agreement with consensus exon-intron junctions and preserve the reading frame. Restriction sites for EcoR I (R), BamH I (B) and Not I (N) are indicated.

Since the cDNAs p2195/p1270 were derived from the AtT-20 tumor cell line there is a potential risk that they harbor mutations which may result in loss or gain of functions not associated with the wild-type form. To rule out this possibility we recloned Bop1 from a plasmid library constructed from whole pituitary tissue of Balb/c mice. To isolate a Bop1 wild-type cDNA, poly(A)$^+$ RNA was obtained from 80 male Balb/c mice (Balb/cAnNCrlBR) and reverse transcription was performed on 5 μg poly (A)$^+$ with a random primer-NotI adapter (5'-ATGTCT-CGAGGCCTTTGCGGCCGCTATANNNNNNNN-3' (SEQ ID NO. 3)). After second-strand synthesis, BstXI adaptors (In-Vitrogen) were added. The cDNAs were digested with Not I, size-selected on a chromaspin column 1000 (Clontech) and cloned into the BstXI/NotI sites of pRK8, a modified pRK5 vector (Spengler et al., Nature 365 (1993), 170–175). Screening of ~0.5×10$^6$ clones with the p2195 cDNA probe allowed the isolation of one full-length cDNA clone designated B-16, which contained a 3.7 kb insert. Transfection of B-16 into LLC-PK1 cells successfully substituted for p2195 or p1270 with respect to regulation of PVR1 expression (data not shown). Entire sequencing of clone B-16 showed a 86 bp non translated 5' region and an extended non translated 3' region of 0.7 kb (FIG. 1B). The coding region of B-16 was identical to p2195 except the reading frame was interrupted at residue 658 by a 630 bp insertion. The sequences at the boundaries of this insertion are in excellent agreement with consensus exon-intron junction sequences and preserve the reading frame (FIG. 1B). We observed this insertion at exactly the same position in clone p1270 derived from the AtT-20 library (FIG. 1B). This finding argues against a cloning artefact in clone B-16 and suggests the presence of an unspliced intron region. In support of this hypothesis, a PCR-based fragment encoding the intron region failed to hybridize to a poly-A$^+$ blot from AtT-20 cells (data not shown). The distribution of Bop1 was assessed by Northern blot of total RNA prepared from different mouse tissues. Interestingly, the anterior pituitary gland displayed by far the highest level of expression of Bop1 mRNA (FIG. 1C). Bop1 gene was expressed at much lower levels in various brain areas including olfactory bulb, cortex, hippocampus, hypothalamus-thalamus, brain stem and cerebellum, while no hybridization was observed in peripheral tissues.

EXAMPLE 2

Constitutive Expression of Bop1 and p53 Abates Growth of Tumor Cells

In order to study the function of Bop1 we aimed to generate clones stably expressing Bop1 protein in the LLC-PK1 cell line. However, independently of the resistance marker employed, we failed to establish a Bop1 -expressing cell clone. To evaluate the possibility that Bop1 inhibits tumor growth we subcloned Bop1 and p53 in sense and anti-sense orientation downstream of a cytomegalovirus promoter in a vector (pCMVPUR) carrying the puromycin resistance gene.

The PCMVPUR sense/antisense constructs (1.0 μg) and pGEM4 filling DNA (3.0 μg) were transfected into 2×10$^6$ into the LLC-PK1 cell line and in addition into the human osteosarcoma cell line Saos-2 (ATCC HTB 85), which was previously shown to be growth-inhibited by wild-type p53 (Diller et al., Mol. Cell. Biol. 10 (1990), 5772–5781). pGEM4 replaced pCMVPUR in mock transfected cells. Three electroporations for each construct were pooled and aliquots were plated in 15 cm culture dishes. The cell lines were grown in DMEM (GIBCO) supplemented with 10% fetal calf serum (GIBCO). Selection with puromycin (5.0 μg/ml) was started 24 hr after transfection. Following transfection, cells were grown with puromycin for 10 days, and the number of viable colonies was scored after incubated with MTT. Data presented in Table I show that introduction of Bop1 sense expression vectors resulted in a substantial suppression of colony formation equivalent to that induced by p53. Abrogation of cell growth by Bop1 or p53 was more prominent in the Saos-2 cell line. In addition the clones that did appear after transfection of Bop1 or p53 sense constructs into the LLC-PK1 cell line died when reexposed to selection after passaging and grew at a slow rate in case further selection was omitted (data not shown).

TABLE I

Bop1 and p53 Suppress the Growth of Tumor Cells

| Cell type | (n) | plasmid | antisense | sense | ratio |
| --- | --- | --- | --- | --- | --- |
| LLC-PK1 | 3 | Bop1 | 1014 ± 170 | 2 | 507 |
|  | 3 | p53 | 1452 ± 258 | 2 | 726 |
|  | 1 | vector | 1653 ± 270 |  |  |
|  | 1 | mock | 0 |  |  |
| Saos-2 | 3 | Bop1 | 2538 ± 354 | 1 | 2500 |
|  | 3 | p53 | 3779 ± 566 | 1 | 3800 |
|  | 1 | vector | 4517 ± 641 |  |  |
|  | 1 | mock | 0 |  |  |

The epithelial cell line LLC-PK1 and the human osteosarcoma cell line Saos-2 were electrotransfected (n=3) with the parent vector pCMVPUR or with vectors encoding sense and antisense Bop1 or wild-type rat p53. pGEM4 carrier DNA replaced pCMVPUR in mock transfected cells. 24 hr later, cells were grown in the presence of 5 μg/ml of puromycin and kept for 10 days with regular medium changes. To score viable colonies cells were incubated with MTT.

EXAMPLE 3

Bop1 and p53 Suppress Growth of Tumor Cells

A system for tetracycline-regulated gene expression was recently described (Gossen and Bujard, Proc. Natl. Acad. Sci. 89 USA (1992), 5547–5551). This system relies on constitutive expression of a tetracycline-controlled transactivator protein (tTA) which activates target genes placed under the control of a regulatory sequence (tetO). Binding of tetracycline (Tc) or its higher affinity derivative anhydrotetracycline (ATc) to tTA prevents activation, whereas activation is achieved by withdrawal of the repressor (Gossen et al., Trends Biotech. 12 (1994), 58–62). In the approach presented here LLC-PK1 and Saos-2 cell lines are transfected with a tTA-encoding vector and isolated one clone from each cell line (L-tTA and S-tTA) which displayed efficient regulation of genes cloned downstream of the tetO sequence (data not shown).

In addition, a new cis-regulatory expression vector was developed with distinct lower basal levels of expression and potent regulatory properties equivalent to or exceeding those exhibited by the original minimal CMV-based expression vector in a panel of host lines attesting to a broad use of this system in future applications, most preferably the study of TSGs. The regulatory region of pUHC13-3 (Gossen and Bujard, Proc. Natl. Acad. Sci. USA 89 (1992), 5547–5551) was excised by HindIII and EcoRI partial digest and inserted into pBlueScript SK(–) digested by EcoRI and HindIII to give pBS-CMVtetO. A fragment of 157 bp encoding the tetO sequence was released by SmaI and inserted into the plasmid pΔMTVLUC (Spengler et al., Nature 365 (1993), 170–175) linearized at +256 bp by HindIII and blunted with T4-DNA polymerase to give the construct pΔMtetOLUC.

The XhoI site (+1) of pΔMtetOLUC was converted into a NotI site by insertion of an oligonucleotide with an internal NotI site. To obtain pΔ5'MtetOLUC a StuI (+863)/NotI (+1) fragment of pΔMtetOLUC was inserted into pBlueScript cut by SmaI/NotI and shortened in size by PpuMI (+786 bp) and EcoRV digestion, blunting and relegation. This fragment was either transferred back into the plasmid pΔMTVLUC using the pBlueScript polylinker HindIII site and the internal BstEII site (+56 bp) or transferred into the plasmid pOP-IPUR by HindIII and NotI digestion to give PMtetO. The vector pOPIPUR is derived from pOPI3CAT (Stratagene) and contains the puromycin gene of pPUR (Clontech) under the control of the SV40 promoter.

Additional copies of the heptameric tetO sequence were isolated from pBS-CMVtetO by SmaI and KpnI digestion and inserted into PMtetOLUC restricted within the tetO sequence by Ecl136II and KpnI. Using this strategy, a series of constructs with increasing numbers of tetO copies was created, which are abbreviated in the following part as PMtetO$_x$LUC with the index displaying the number of copies of the heptamer tetO.

Target cDNAs were inserted downstream the ΔMtetO sequences via the unique Not I site. For stable transfections the plasmids p3'SStTA, PMtetO$_5$Bop1 and PMtetO$_5$p53 were linearized with Eam1105I and 1 μg of DNA was co-transfected with 3 μg pGEM4 filling DNA into 2×10$^6$ cells. Selection of tTA-cell clones started 24 hr after transfection using hygromycin (MERCK) at a concentration of 700 μg/ml and 500 μg/ml in LLC-PK1 and SaOs-2 cells, respectively. Selection for clones expressing the Bop1 gene or p53 was carried out at a concentration of 5.0 μg/ml puromycin. The following numbers of clones were screened: L-tTA: Bop1=95, p53=92 and S-tTA: Bop1 n=77, p53: n=72. All the clones revealed impaired cell growth to varying degrees under the activated state (–ATc), which was microscopically scored twice during seven days. For each condition one half of the most promising clones was subjected to additional rounds of analysis with about 10 clones remaining at the fourth round.

Three candidate clones from each transfection condition were subjected to a preliminary analysis of counts of cell numbers (data not shown). The LLC-PK1- and Saos-2-derived clones (L-Bop and L-p53, S-Bop and S-p53, resp.) displaying the greatest differences in growth were further analyzed (FIG. 2A). Importantly, no major differences in the growth behavior were observed in the presence of the repressor ATc between Bop1—and p53-expressing clones and the parent clones L-tTA and S-tTA (FIG. 2A). Therefore the differences in cell counts on day six were primarily due to the suppression of growth in the absence of the repressor. Measurement of proliferation rate revealed that Bop1 (L-Bop: 11-fold; S-Bop: 20-fold) was slightly less potent than p53 (L-p53: 15-fold; S-p53: 25-fold) in reducing the growth rate of both cell lines. Western blot analysis proved that Bop1 protein was not detectable in L-Bop or S-Bop cells in the presence of ATc. A strong increase in protein levels of Bop1 was noted in the activated state (data not shown and FIG. 5B). Similar results were also obtained for the regulation of p53 in Saos-2 and LLC-PK1 cells (data not shown and FIG. 5B). These results emphasize that the modified expression vector combines low basal activity with potent regulatory properties.

Figures 2, 2B:
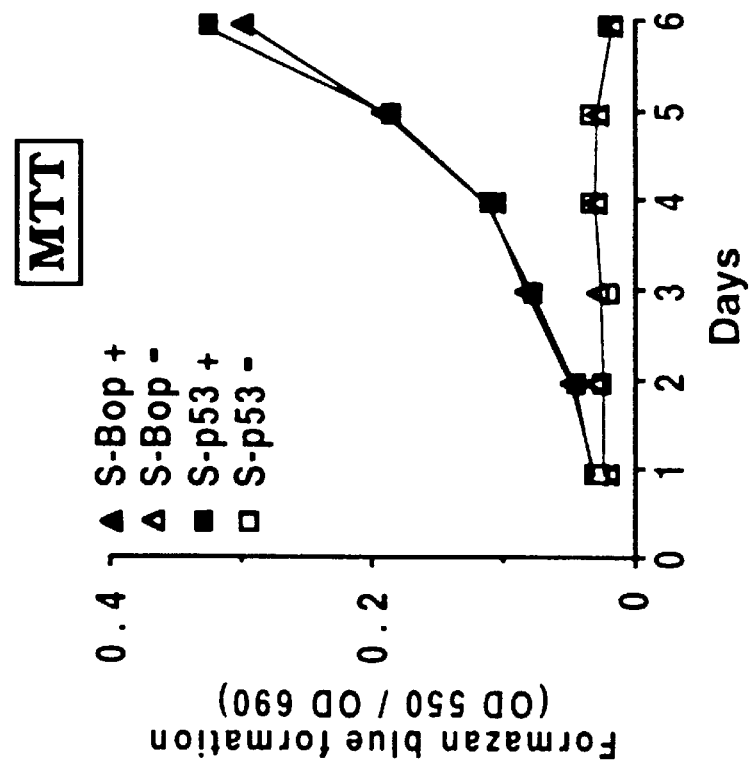
Figures 1, 2B:
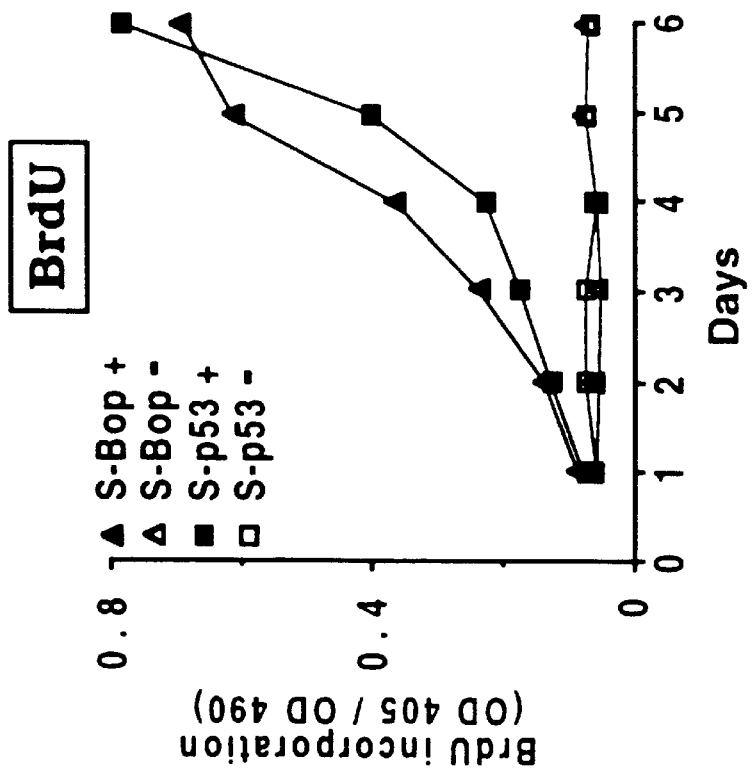

Total counts of cell numbers do not necessarily discriminate between alteration of cell proliferation and viability. It was therefore decided to evaluate the effects of Bop1 and p53 expression by two complementary methods. First, DNA-synthesis was studied with a non-radioactive immunoassay based on incorporation of 2-bromodeoxyuridine (BrdU) into nuclear DNA on each of six days with or without ATc (FIG. 2B). Second, it was measured the conversion of the tetrazolium salt MTT to formazan blue, which depends on the activity of mitochondrial and cytoplasmatic dehydrogenases. This activity depends on cell viability and closely correlates with cell proliferation (FIG. 2B).

The counts of Cell Numbers, 2-Bromodeoxyuridin incorporation and Formazan production were performed as follows:

Equal number of cells (5,000) were seeded in 24-well plates in DMEM/10% FCS supplemented with ATc (10$^{-11}$ μg/ml). After recovery for 36 hr, medium was renewed and the repressor omitted for half of the samples. For samples lacking the repressor, the medium was changed again 3 hr later to remove residual amounts of ATc. Growth medium was changed routinely on day 3. Average cell counts from 3 to 5 experiments in triplicate are plotted versus time after removal of the repressor. For measurement of DNA-synthesis cells (1,000) were seeded in 48-well plates and cultured as outlined above. On each of six days, 10 μM 2-bromodeoxyuridin was added for 8 hr and subsequent steps were carried out according to the manufacturer's instructions (Boehringer Mannheim). For measurement of cell viability, 1,000 cells were seeded in 24-well plates and cultured as described above. The average of OD measurements for DNA-synthesis and cell-viability was obtained from three experiments performed in triplicates. To test serum-independence, cells were kept in normal medium for 36 hr before serum was washed out once with DMEM and replaced by DMEM/0.1% FCS/±ATc.

Figure 2D:
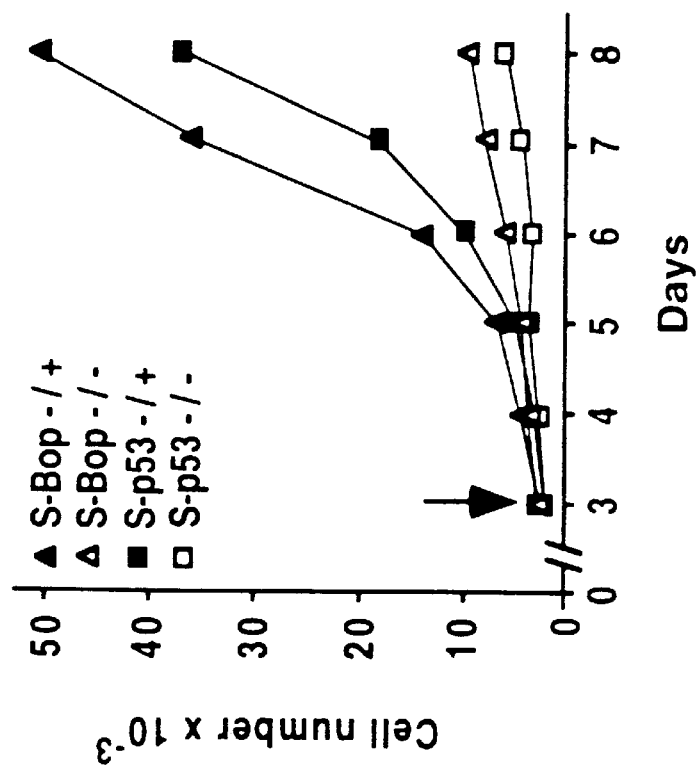
Figure 2C:
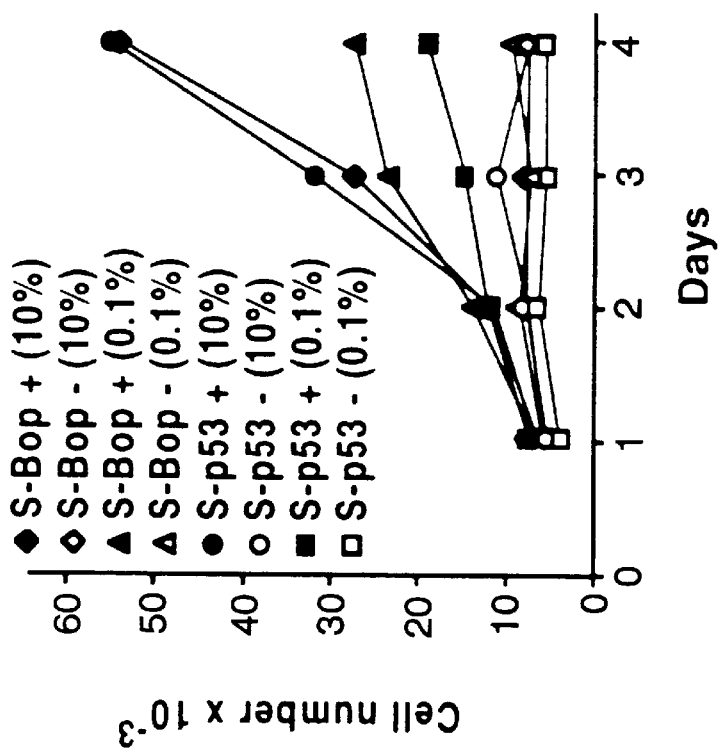

The results obtained for S-Bob and S-p53 emphasize the observed differences in cell counts (FIG. 2A), which correlate with those obtained in overall cell proliferation and overall viability measurements (FIG. 2B). Similar results were obtained for L-Bop and L-p53 (data not shown). Cells from LLC-PK1 (data not shown) and Saos-2 clones kept under low serum conditions (0.1% FCS) in the repressed state displayed reduced growth rate and cell death from day three on, indicating serum-dependence to maintain logarithmic growth (FIG. 2C). In contrast, proliferation under expression of Bop1 and p53 remained unchanged (FIG. 2C). Therefore, inhibition of tumor growth by Bop1 and p53 proceeds through mechanisms unrelated to the presence of serum factors in these cellular models.

The ability of Bop1 to suppress growth could be due to a non-specific lethal effect of protein overproduction, resulting in cell death. Alternatively, it could be a manifestation of a more specific effect on cell proliferation. To further investigate these two possibilities, the growth pattern following reexposure to ATc of the surviving cells was tested. The impairment of cell growth by Bop1 and p53 expression was transient for both the LLC-PK1 (data not shown) and Saos-2 clones studied. Reexposure to the repressor ATc caused cells to resume logarithmic growth after 48 hr (FIG. 2D). Therefore, Bop1- and p53-induced changes in cell growth were not permanent and at least in part reversible, arguing against a non-specific effect of protein overproduction.

EXAMPLE 4

Bop1 and p53 Inhibit Soft-Agar Colony Formation

Anchorage-independent growth is often correlated with tumorigenesis and is a strong criteria for cultured cell transformation. To test the influence of Bop1 or p53 on anchorage-independent growth, LLC-PK1 and Saos-2 cell clones were assayed for their ability to grow in soft-agar. Each well (35-mm) of a six-well culture dish was coated with 4 ml of bottom agar mixture (DMEM/10% FCS/0.6% agar/±ATc). After the bottom layer had solidified, 2 ml of top agar mixture (DMEM/10% FCS/0.3% agar/±ATc) containing the cells was added. ATc was used at a final concentration of $3 \times 10^{-11}$ μg/ml. After 7 days, another 1.5 ml top agar mixture (±ATc) was added. On day 10, the wells were overlaid with 2 ml MTT (1 mg/ml) and incubated for an additional 4 hr, washed once with PBS and then photographed. Colony formation by Bop1 or p53 expressing cells (−) was dramatically reduced compared to the repressed state (+) (FIG. 3). Also the few colonies formed under Bop1 or p53 expression were of smaller size. These results demonstrate that Bop1 and p53 can abate anchorage-independent growth of tumor cells, one of the hallmarks of tumorigenicity.

EXAMPLE 5

Bop1 and p53 Suppress Tumor Formation in Nude Mice

The most stringent experimental test of neoplastic behavior is the ability of injected cells to form tumors in nude mice. Yet, not all of the altered cellular growth properties commonly associated with the transformed state in-vitro are required for neoplastic growth in-vivo and vice versa. Therefore loss of tumorigenicity under expression of Bop1 in-vivo would be a critical test to substantiate the tumor suppressor function of Bop1. To achieve gene regulation by Tc in nude mice, half of the animals were implanted with Tc pellets whereas the remainder were implanted with placebo pellets. 36 nude mice were randomly distributed into three groups of 12 animals. In each group, half of the animals were subcutaneously implanted with Tc pellets (63 mg; 0.7 mg tetracycline hydrochloride per day; Innovative Research of America) and the remaining half were implanted with the placebo pellets (Innovative Research of America). Two days latter, each animal was injected subcutaneously on each side with S-Bop or S-p53 cells which were grown in the presence of ATc, trypsinized and resuspended in PBS at a density of $5 \times 10^7$ cells/ml. 100 μl of this cell suspension was injected subcutaneously into each side of each animal grown in the continuous presence of ATc. Two groups were injected with S-Bop cells from two independent trypsinizations whereas one experiment was performed with S-p53 cells. Due to the clonal origin of S-Bop and S-p53, differences in the tumorigenicity of each clone were observed as inferred from the difference in the observed lag in tumor formation which was assessed at 11 weeks after cell injection for S-Bop and at 16 weeks for S-p53. S-Bop- and S-p53-injected animals were sacrificed at 11 and 16 weeks, respectively, dissected and the tumors were weighed. Table II presents results from two experiments with S-Bop (Bop1) and one experiment with S-p53 (p53). In agreement with previous results (Chen et al., Science 250 (1990) 1576–1580), p53 expression impaired tumor formation by Saos-2 cells in-vivo. Interestingly, Bop1 was as efficient as p53 in inhibiting tumor formation as deduced from tumor incidence (Table II) and from the average tumor weight (193±13 mg (n=14) for Tc vs. 18±7 mg (n=2) for placebo). Conclusively, Bop1 and p53 are equipotent at inhibiting tumor formation in-vivo.

TABLE II

Bop1 and p53 Inhibit Tumor Formation in-vivo

| clone | tumor incidence (No. of tumor-bearing injection sites/ total No. of injection sites) | |
|---|---|---|
| | placebo | Tc |
| S-Bop (Bop1) exp. n°1 | 2/12 | 14/14 |
| S-Bop (Bop1) exp. n°2 | 1/12 | 12/12 |
| S-p53 (p53) | 1/12 | 10/12 |

Nude mice were implanted with placebo or Tc pellets subcutaneously. Two days latter, $5 \times 10^6$ cells from each clone were injected subcutaneously into each side of each animal, and tumor formation was scored at 11 weeks for S-Bop (Bop1) and 16 weeks (p53).

EXAMPLE 6

Expression of Bop1 and p53 Induce Apoptosis

Two days following induction of p53 expression, Saos-2 cells flattened and greatly enlarged (three to eight fold) in average diameter, which was most evident when grown in small clusters. Similar changes, though less prominent (two to fourfold increases in the average diameter), were also observed for L-p53 (data not shown). In contrast, Bop1 expressing LLC-PK1 or Saos-2 clones appeared indistinguishable from the parent cell lines giving a first hint of functional differences between Bop1 and p53. Yet, an increasing number of cells with signs of lost cell viability was observed from day two onwards following Bop1 or p53 expression. These cells failed to convert MTT, shrank in size, were abundant in phase contrast microscopy, revealed membrane blebbing, and rounded further up before detaching from the plates. For Bop1 these alterations were most evident in Saos-2 cells (S-Bop) and for p53 in LLC-PK1 cells (L-p53) (data not shown) and appear reminiscent of an apoptotic cell death. This form of cell death is often accompanied by fragmentation of the DNA into a ladder of regular subunits.

To address this question LLC-PK1 and Saos-2 cells were seeded with (4,000 cells/cm$^2$) or without (8000 cells/cm$^2$) ATc for 3 days and soluble DNA was prepared as described (Hockenbery et al., Nature 348 (1990), 334–336). Aliquots of DNA were fractionated on a 1.2% agarose gel. When the repressor was omitted a clearly visible degradation into oligonucleosomal DNA fragments became evident (FIG. 4A), which was most advanced following expression of Bop1 in Saos-2 cells.

The fluorescent DNA-stains ethidium bromide and acridine orange were employed to examine nuclear changes under the ATc-deprived condition. Therefore, the cells ($5 \times 10^4$) were seeded in the absence of ATc in 12-well clusters and grown for three days. After aspirating the medium, the cells were washed twice with PBS and overlaid with a staining mix of ethidium bromide (50 μg/ml) and acridine orange (10 mg/ml) for 10–20 min. Photography was carried out using UV-filters of 400–420 nm and of 510–550 nm.

Since the flattened and enlarged cell shape of p53-expressing cells enhanced attachment to the plastic surface, a comparable large population of cells exhibited nuclear signs of apoptosis, whereas Bop1-expressing cells shrank, dislodged quickly and appeared less represented in these experiments (data not shown). The structural changes of nuclear demise following Bop1 expression were even more evident when floating cells were collected and subjected to analysis (FIG. 4B). Decay of the nucleus involved nuclear shrinkage, condensation of the chromatin, collapse into patches and then into crescents in tight apposition to the nuclear envelope, and finally in one or several dense spheres (FIG. 4B).

To investigate the extent of DNA-damage, terminal deoxynucleotidyl transferase-mediated nick end labeling (TUNEL) was performed using the ApopTag kit (Oncor), according to the manufacturer's instructions, followed by flow cytometry. The cells were seeded with (1,800 cells/cm$^2$) or without (3,600 cells/cm$^2$) ATc for 3 days. Then the cells were pelleted, kept on ice for at least 10 min and resuspended in 900 μl of propidium iodide staining solution (PISS=50 μg/ml propidium iodide; 0.1% trisodium citrate dihydrate; 0.1 mg/ml RNase A; 0.1% Triton X-100). Following an overnight incubation, cell cycle phase distribution was determined with FACScan (Becton-Dickinson) with 20,000 events analyzed using Modfit software (Verity Software House, Inc.). Incubation of each clone in the absence of ATc induced a large increase in the number of cells with enhanced or high fluorescence indicative of free DNA ends and nuclear-fragmentation (FIG. 4C). These results confirm the data obtained with ethidium bromide-stained gels and indicate that the proportion of cells displaying nuclear damage was as high as 60–70% following expression of either Bop1 or p53.

Taken together these experiments give convincing evidence that Bop1 and p53 recruit apoptotic programs to inhibit growth of tumor cells and Saos-2 cells seem highly apoptosis proficient following expression of Bop1.

EXAMPLE 7

Expression of Bop1 and p53 Induces Changes in Cell Cycle Distribution

To characterize further the mechanisms by which Bop1 might regulate cell growth the distribution of cell cycle phases was studied. Increases in wt p53 levels are known to suppress cell growth by blocking the cell cycle at the G1 to S transition (Hunter and Pines, Cell 79 (1994), 573–582; Sherr and Roberts, Genes and Dev. 91 (1995), 1149–1163). More recently p53 has been suggested to address an additional checkpoint by arresting cells at the G2/M boundary (Agarwal et al., Proc. Natl. Acad. Sci. USA 92 (1995), 8493–8497; Cross et al., Science 267 (1995), 1353–1356; Stewart et al., Oncogene 10 (1995), 109–115; Yamato et al., Oncogene 11 (1995), 1–6). In control experiments, the parent clones L-tTA and S-tTA showed no difference in the distribution of cells in different phases of the cycle in the absence or presence of ATc (data not shown). In contrast, expression of Bop1 reduced the proportion of S-Bop populations in S phase and G2/M phase from 37.8% and 17.5% to 24.5% and 12.6%, respectively. Importantly there was a clear compensatory increase of cell populations in G1 from 44.7% for the repressed state to 63.0% for the expressed state of S-Bop (FIG. 5A).

The results obtained for p53 expression in the S-p53 cell clone are in agreement with those obtained recently with a temperature-sensitive mutant p53 in Saos-2 cells (Yamato et al., Oncogene 11 (1995), 1–6). A decrease in G1 and S phase from 39.4% to 31.8% and from 43.7% to 35.0% was observed and a clear increase in G2/M from 16.9% to 33.2%. (FIG. 5A). The failure of p53 to proceed to a G1 arrest reflects most likely the presence of the deleted non-functional retinoblastoma gene product (Rb) in the Saos-2 cell line.

These observations were extended to the LLC-PK1 cell line and though shifts of populations in cell cycle phases under expression of Bop1 and p53 were less prominent than in the Saos-2 cell clones, there was again a clear increase in G1 phase populations for expression of Bop1 (G1 59.1% vs. 43.7%; S 28.2% vs. 38.9%; G2/M 12.7% vs. 17.4%) and a shift for G2/M populations under p53 (G1: 39.3% vs. 44.1%; S: 32.1% vs. 40.2%; G2/M: 28.6% vs. 15.7%) (data not shown).

p53 achieves G1 arrest through transactivation of the gene encoding the cyclin-dependent kinase inhibitor p21 (also designated Cip1, Waf1, Sdi1, Cap20). Increased levels of p21 inhibit the kinase activity of cdk2 and maintain Rb in its underphosphorylated state in tight association with members of the E2F family. As a result, transactivation of genes driving the cell cycle is inhibited (Goodrich et al., Cell 67 (1991), 293–302; Weinberg, Cell 81 (1995), 323–330). The question arose whether Bop1-induced G1 arrest utilizes the same molecular pathway as p53. Expression of p53 in Saos-2 cells resulted in a strong induction of the p21 protein proving an intact and efficient transactivation of the endogenous gene by the exogenous p53 protein (FIG. 5B). Yet, no regulation of the p21 gene in Saos-2 cells was encountered following expression of Bop1 (FIG. 5B). The same results were obtained in the LLC-PK1-clones with a strong induction of p21 by p53 (data not shown). Conclusively, Bop1 induces G1 arrest in these cellular models through molecular relays independent of p21.

In a number of cellular systems, wt p53 activation has been shown to confer growth arrest (Mercer et. al., Proc. Natl. Acad. Sci. USA 87 (1990), 6166–6170; Merlo et al., Oncogene 9 (1994), 443–453; Michalovitz et al., Cell 62 (1990), 671–680; Roemer and Friedmann, Proc. Natl. Acad. Sci. USA 90 (1993), 9252–9256). In contrast, wt p53 failed to cause a measurable arrest in M1 cells and cell cycle progression proceeded while viability was lost within 48 hr (Yonish-Rouach et al., Mol. Cell. Biol. 13 (1993) 1415–1423; Yonish-Rouach et al., Nature 352 (1993) 345–347). In that system, cells in G1 appeared to be preferentially susceptible to the death-inducing activity of wt p53. Therefore the question arose whether in the used cellular models, in which Bop1 and p53 play a dual role in regulation of apoptotic cell death and cell cycle progression, a particular phase of the cycle is associated with protection or increased susceptibility to cell death. To address this issue the cell cycle analysis was extended and double staining with propidium iodide was performed to measure DNA content and TUNEL to assess apoptosis. As shown in FIG. 5C, apoptotic cells proceeded from each phase of the cell cycle as indicated by the distribution of DNA content of apoptotic cells. It was concluded that cell cycle arrest is not a prerequisite to apoptosis and that both Bop1 and p53 induced apoptosis through a pathway which is independent of the one involved in cell cycle arrest.

EXAMPLE 8

Bop1 is a Nuclear Transcription Factor

Figure 6A:
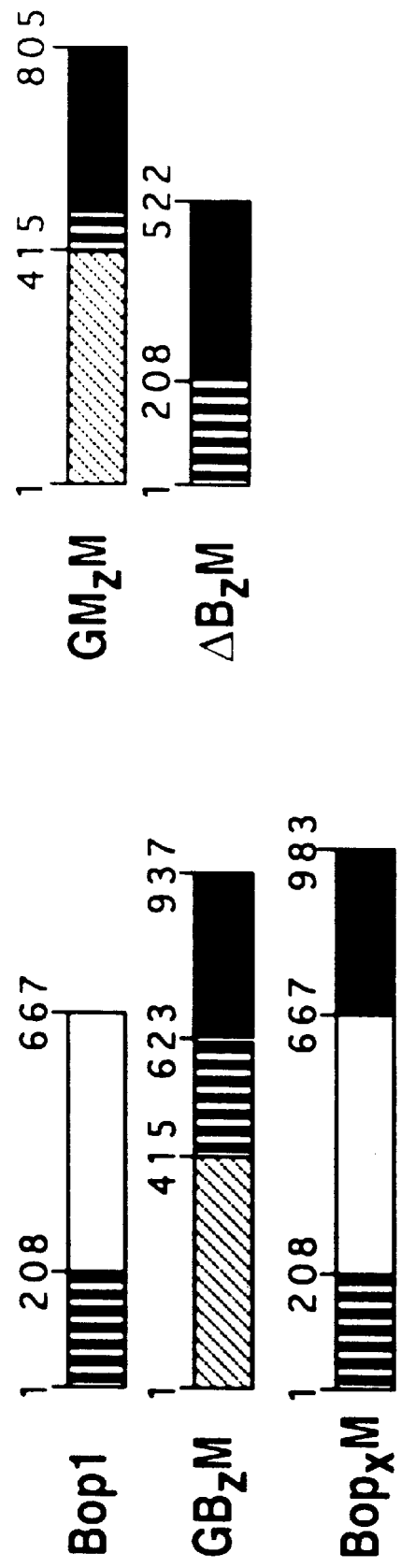
Figures 2, 6B:
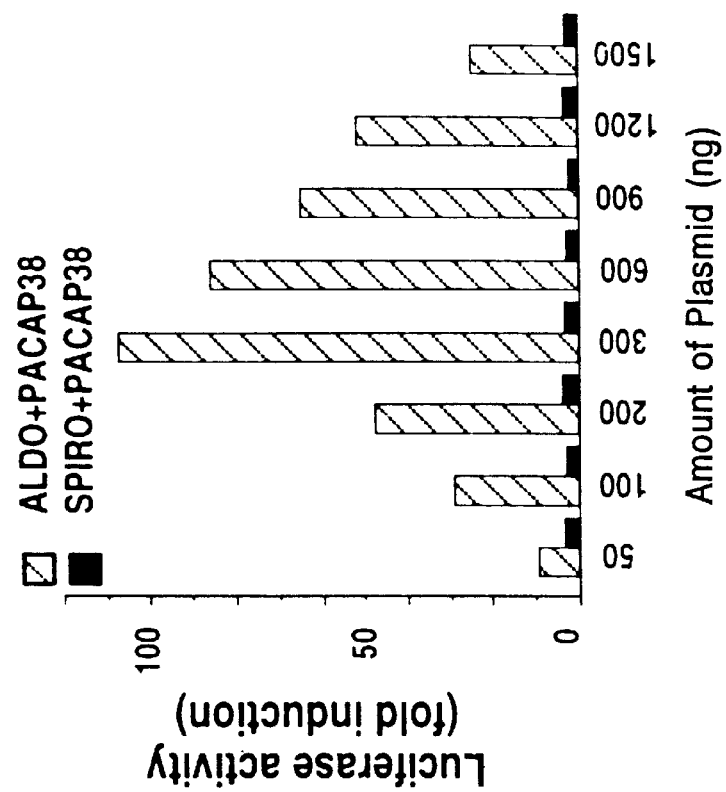
Figures 1, 6B:
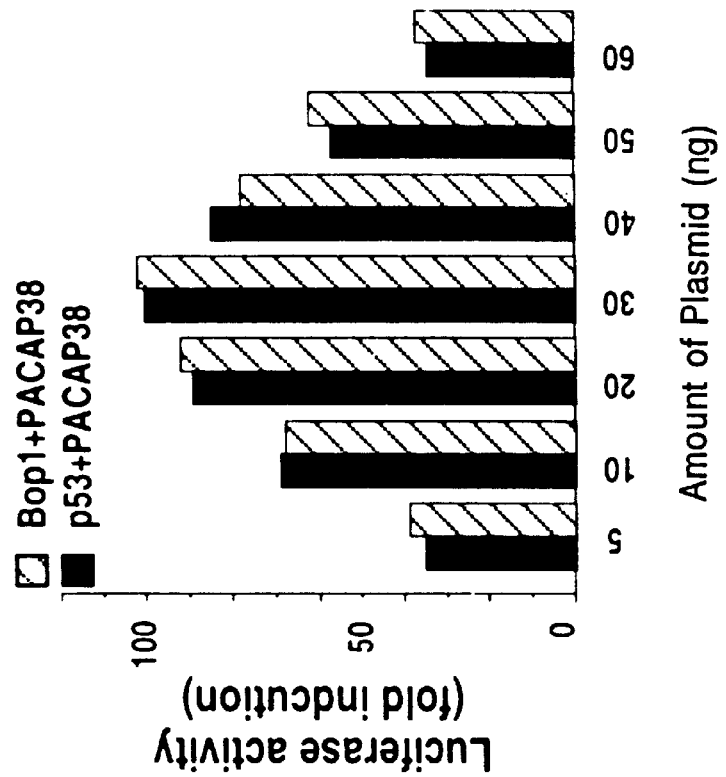

Structural analysis of Bop1 demonstrated features compatible with a transcription factor composed of a N-terminal seven zinc finger DNA-binding domain and a COOH-terminal transactivation domain. Without information on the actual cis-regulatory sequences recognized by Bop1 to trans-activate target genes, it was decided to use the induction of the endogenous PVR1 gene as a model to dissect functional domains of Bop1. A bimodal regulation of the PVR1 gene was observed, indistinguishable for Bop1 and wt p53 cDNAs as measured by induction of the cAMP-sensitive luciferase gene (FIG. 6B). The decrease in PVR1 expression with high amounts of cDNAs was unrelated to cellular toxicity. The two-zinc finger domain of the hybrid steroid receptor $GM_ZM$ (Rupprecht et al., Mol. Endocrinology 7 (1993), 597–603) was replaced with the seven-zinc finger domain of Bop1 ($B_Z$) to create $GB_ZM$ (FIG. 6A).

The hormone-binding domain of the mineralocorticoid receptor was replaced in this construct to avoid possible pleiotropic effects associated with glucocorticoids.

The $GR_{NX}$, $MR_{NX}$ and $GM_ZM$ constructs were previously described (Rupprecht et al., Mol. Endocrinology 7 (1993), 597–603). Primers used to create $GB_ZM$ were:

5'-gtgatggcggccgCCATTCCGCTGTCAAAAATGTG-3' (+7 bp to +27 bp) (SEQ ID NO.10)

and 5'-ccgcgccctcgagGGTCTTCTTGGTGTGACG-3' (+618 bp to +601 bp) (SEQ ID NO.11).

The different constructs were subcloned into pRK5PUR. To create the construct $\Delta B_ZM$, the GR-transactivation domain and part of the Bop1 zinc finger binding domain was excised from $GB_ZM$ by EcoRI/MluI digestion and replaced by the restriction fragment EcoRI/MluI (−541 bp to +272 bp) of p2195.

Primers used to create $Bop_ZM$ were:

5'-gcggccgCAGAGCCGTCTTTCACTC-3' (+1148 bp to +1166 bp) (SEQ ID NO. 12) and

5'-ccgcgcctcgagAACTGTCCATTTCTTATAGAC-3' (+2001 bp to +1980 bp) (SEQ ID NO. 13).

The stop codon of p2195 was replaced by the amino acid histidine (CTC) as part of the XhoI site used to ligate to the MR-hormone binding domain. PCR-generated fragments were sequenced to verify accurate amplification.

In transfection of LLC-PK1 cells ($2\times10^6$), pGEM4 plasmid was used as carrier and the amount of pRK expression vector was kept constant with pRK5CAT. Luciferase activity was determined as previously described (Spengler et al., Nature 365 (1993), 170–175) 12 hours after transfection.

The Bop1/steroid-receptor hybrid gene $GB_ZM$ was co-transfected with the cAMP-responsive reporter pΔMC16LUC into LLC-PK1 cells. Aliquots of transfected cells were incubated either with the mineralocorticoid receptor antagonist spironolactone or the agonist aldosterone and PACAP was added to both conditions after 12 hr (FIG. 6B). Though the transactivation potency of $GB_ZM$ was 10-fold less compared to the native Bop1 cDNA, a bimodal induction of the $PVR_1$ gene for increasing amounts of $GB_ZM$ was consistently observed, which closely paralleled the one observed for Bop1 and p53. In contrast the construct $\Delta B_ZM$, which lacks the glucocorticoid receptor transactivation domain failed to confer regulation of PVR1, implicating an active transcriptional mechanism underlying this response (FIG. 6C). No regulation of the PVR1 gene was observed for the transfected parent construct $GM_ZM$ (data not shown).

Further support for the role of Bop1 as a nuclear transcription factor was obtained with the fusion protein $Bop_XM$, in which the C-terminus of Bop1 was linked with the hormone-binding domain of the mineralocorticoid receptor (FIG. 6A). Transfection of this construct into LLC-PK1 cells completely prevented transactivation of the PVR1 gene in the absence of mineralocorticoid receptor ligands. In contrast aldosterone and spironolactone allowed efficient regulation of the PVR1 gene (FIG. 6C). The activation of $Bop_XM$ by the aldosterone antagonist spironolactone supports the view that the attached hormone-binding domain merely serves to trap this fusion protein to cytoplasmatic heat shock proteins (Picard, Trends Cell Biol. 3 (1993), 278–280) and does not interfere otherwise with the functions of Bop1. In contrast, release of Bop1 from this cytoplasmatic anchor by either aldosterone or spironolactone allowed nuclear translocation and transactivation of Bop1 targeted genes.

Moreover, to prove nuclear localization of Bop1 immunocytochemistry on S-Bop cells was performed with an antiserum that was raised against a Bop1 fusion protein truncated for the zinc finger domain (GST-BopΔZF).

Figures 1, 6D:
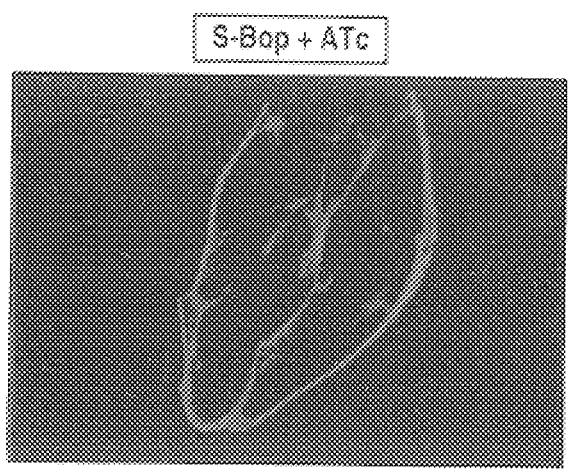
Figures 2, 6D:
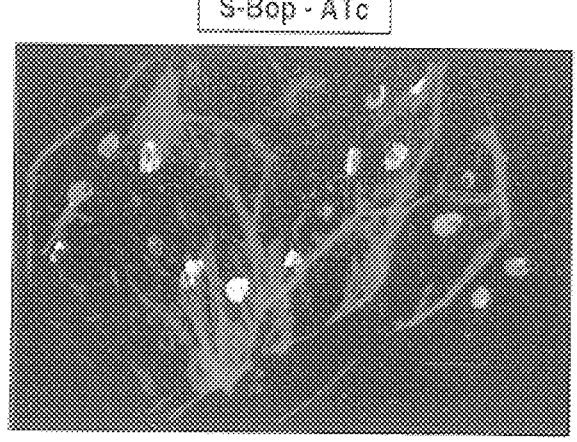

The plasmid encoding the GST-BopΔZF fusion protein was constructed by a partially digesting the plasmid pRK8-p2195 with BstX I, blunt-ending with T4 DNA polymerase and digesting with Not I. The resulting 0.9 kb fragment was subcloned into pGEX-5X-3 (Pharmacia) previously digested with Sma I and Not I. The fusion protein was purified by affinity chromatography using glutathione-sepharose beads followed by SDS-PAGE and electroelution. Rabbits were immunized with 40 μg of the fusion protein and antisera were collected on a weekly basis. Purified IgG were used for western blots and immunocytochemistry experiments. Western blots were performed on total cell lysates (50 μg) with the above-mentioned purified IgG or with commercially available antibodies to p53 (Pharmingen, San Diego, USA catalog #14091A), $p21^{Waf1}$ (Transduction laboratories, Lexington, USA, catalog #C24420), $p27^{Kip1}$ (Transduction laboratories, catalog #K25020) and $p16^{ink4}$ (Santa Cruz Biotechnology, Inc., Santa Cruz, USA, catalog #sc-759). Immunocytochemistry, and labeling and staining of actin filaments with rhodamine-conjugated phalloidin were performed as previously described (Ibarrondo et al., Proc. Natl. Acad. Sci. USA 92 (1995), 8413–8417). As shown in FIG. 6D, no Bop1 immunoreactivity was detected in the presence of ATc whereas an intense nuclear immunostaining was seen in the absence of Atc.

A nucleic acid molecule prepared by the process described herein is exemplified by a culture deposited in the culture collection Deutsche Sammlung von Mikroorganismen und Zellkulturen GmbH in Braunschweig, Germany on Aug. 12, 1996, and identified as:

pBluescript II SK(−) p2195 (NotI).

This culture was assigned accession number DSM 11112.

The present invention is not to be limited in scope by the specific embodiments described which are intended as single illustrations of individual aspects of the invention, and any nucleic acid molecules, proteins, constructs or antibodies which are functionally equivalent are within the scope of this invention. Indeed, various modification of the invention in addition to those shown and described herein will become apparent to those skilled in the art from the foregoing description and accompanying drawings. Such modifications are intended to fall within the scope of the appended claims.

We claim:

1. A nucleic acid molecule encoding a protein having the biological activity of a tumor suppressor selected from the group consisting of:
  (a) nucleic acid molecules encoding for a polypeptide comprising the amino acid sequence given set forth in SEQ ID NO.2;
  (b) nucleic acid molecules comprising the nucleic acid sequence given in SEQ ID NO.1;
  (c) nucleic acid molecules specifically hybridizing to a nucleic acid molecule as defined in (a) or (b); and
  (d) nucleic acid molecules, the nucleotide sequence of which is degenerate as a result of the genetic code to a nucleotide sequence of a nucleic acid molecule as defined in (c).

2. A method for the identification and cloning of nucleic acid molecules encoding a protein having the biological activity of a tumor suppressor comprising the steps of:
  (i) transfecting mammalian cells with
    (a) a first vector comprising a scorable reporter gene operatively linked to regulatory elements comprising at least one cAMP responsive element so located relative to said reporter gene to permit cAMP inducible expression thereof; and
    (b) pools of expression vectors comprising nucleic acid molecules linked to regulatory elements allowing expression in the mammalian cells;
  (ii) cultivating the transfected cells under conditions which permit expression of the nucleic acid molecules present in the vectors;
  (iii) identifying those vector pools which lead after transfection to expression of said reporter gene in the mammalian cells; and
  (iv) isolating from the so-identified vector pools the nucleic acid molecule present in the vectors and testing its product for tumor suppressor activity.

3. The method of claim 2, further comprising after step (iii) subdividing any vector pools identified in step (iii) and repeating steps (i) to (iii) until the vector pool identified in step (iii) only comprises a limited number of vectors, said vectors differing with respect to nucleic acid molecules present in the vectors.

4. The method of claim 2, wherein in step (ii) a ligand of a receptor which is capable of increasing the level of intracellular cAMP is added to the culture medium.

5. The method of claim 4, wherein the ligand is the peptide pituitary adenylate cyclase activating peptide (PACAP).

6. The method of claim 2, wherein the mammalian cells are LLC-PK1 cells (ATCC CC101) or Saos-2 cells (ATCC HTB 85).

7. The method of claim 2, wherein the cAMP responsive element is derived from a corticotropin releasing hormone gene.

8. The method of claim 2, wherein the regulatory elements controlling the reporter gene are derived from mammary mouse tumor virus (MMTV).

9. The method of claim 2, wherein the reporter gene codes for a luciferase.

10. The method of claim 2, wherein the nucleic acid molecules present in the vectors of the vector pool are cDNAs.

11. The method of claim 9, wherein the cDNA is prepared from RNA obtained from mammalian, bacterial, fungal or plant cells or viruses.

12. A nucleic acid molecule obtainable by a method of claim 2 which encodes a protein having tumor suppressor activity.

13. A nucleic acid molecule which specifically hybridizes to the nucleic acid molecule of claim 1 which encodes a mutated version of the protein which has lost its tumor suppressor activity.

14. The nucleic acid molecule of claim 1, which is DNA.

15. The nucleic acid molecule of claim 14 which is cDNA.

16. The nucleic acid molecule of claim 1, which is derived from a mammal.

17. The nucleic acid molecule of claim 16, wherein the mammal is mouse.

18. The nucleic acid molecule of claim 16, wherein the mammal is human.

19. A vector comprising a nucleic acid molecule of claim 1.

20. The vector of claim 19, wherein the nucleic acid molecule is operatively linked to regulatory elements permitting expression in prokaryotic or eukaryotic host cells.

21. A host cell comprising a vector of claim 19.

22. The host cell of claim 21, which is a bacterial, fungal, plant or animal cell.

23. The host cell of claim 22, which is a mammalian cell.

24. Method for the production of a polypeptide having the biological activity of a tumor suppressor comprising culturing a host cell of claim 22 under conditions allowing the expression of the polypeptide and recovering the produced polypeptide from the culture.

* * * * *